(12) United States Patent
Sato et al.

(10) Patent No.: US 12,064,091 B2
(45) Date of Patent: Aug. 20, 2024

(54) IMAGE SYSTEM, ENDOSCOPE SYSTEM, LIGHT SOURCE DEVICE, AND CONTROL METHOD FOR LIGHT SOURCE DEVICE

(71) Applicant: OLYMPUS CORPORATION, Tokyo (JP)

(72) Inventors: Takayuki Sato, Tokyo (JP); Satoshi Tanaka, Tokyo (JP); Masahiro Nishio, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 363 days.

(21) Appl. No.: 17/518,994

(22) Filed: Nov. 4, 2021

(65) Prior Publication Data
US 2022/0057623 A1   Feb. 24, 2022

Related U.S. Application Data

(63) Continuation of application No. PCT/JP2019/018601, filed on May 9, 2019.

(51) Int. Cl.
*A61B 1/06* (2006.01)
*G02B 23/24* (2006.01)

(52) U.S. Cl.
CPC .......... *A61B 1/0655* (2022.02); *A61B 1/0661* (2013.01); *G02B 23/2461* (2013.01); *G02B 23/2484* (2013.01); *G02B 23/2492* (2013.01)

(58) Field of Classification Search
CPC ............... A61B 1/0655; A61B 1/0661; G02B 23/2461; G02B 23/2484; G02B 23/2492; H04N 23/70
See application file for complete search history.

(56) References Cited

U.S. PATENT DOCUMENTS

| | | | | |
|---|---|---|---|---|
| 10,225,446 B2* | 3/2019 | Sakai | ..................... | G02B 23/26 |
| 2014/0203170 A1* | 7/2014 | Ono | ..................... | A61B 1/0661 |
| | | | | 250/208.1 |
| 2014/0275783 A1* | 9/2014 | Blanquart | .......... | A61B 1/00066 |
| | | | | 600/112 |
| 2014/0371535 A1* | 12/2014 | Seto | ................... | G02B 23/2484 |
| | | | | 600/160 |
| 2015/0116561 A1* | 4/2015 | Takei | ..................... | G03B 15/05 |
| | | | | 348/296 |
| 2016/0353972 A1* | 12/2016 | Yano | ................ | A61B 1/000094 |

FOREIGN PATENT DOCUMENTS

| | | |
|---|---|---|
| JP | 5989284 B1 | 9/2016 |
| JP | 2017-023771 A | 2/2017 |

OTHER PUBLICATIONS

Jul. 23, 2019 Search Report issued in International Patent Application No. PCT/JP2019/018601.

* cited by examiner

*Primary Examiner* — John W Miller
*Assistant Examiner* — Humam M Satti
(74) *Attorney, Agent, or Firm* — Oliff PLC

(57) ABSTRACT

An imaging system includes a lighting controller for independently controlling emission of illumination light to be emitted by a light source in: (i) a non-all-line exposure period, which contains a reading period in which electrical signals are sequentially read out on a horizontal-line basis from an image sensor for one frame or one field period, and in which at least one horizontal line of the horizontal lines for the one frame or the one field period is not exposed to light, and (ii) in an all-line exposure period, in which all of the horizontal lines for the one frame or the one field period are exposed to light.

21 Claims, 15 Drawing Sheets

| TYPE OF ENDOSCOPE SCOPE | A | B |
|---|---|---|
| UPPER LIMIT OF PERMISSIBLE TEMPERATURE | TA | TB |
| TEMPERATURE OF TIP PORTION WHEN ILLUMINATION LIGHT OF MAXIMUM LIGHT AMOUNT BM WHICH CAN BE EMITTED BY LIGHT SOURCE DEVICE IS PROVIDED | TMA | TMB |
| MAGNITUDE RELATION | TA＞TMA | TMB＞TB |
| MAXIMUM VALUE BX OF ILLUMINATION LIGHT AMOUNT | BX=BM | BM＞BX |
| MAXIMUM VALUE I OF CURRENT TO BE APPLIED TO LIGHT SOURCE | I=I3 | I=I5 (I3＞I5＞I4) |

Fig. 13

IMAGE SYSTEM, ENDOSCOPE SYSTEM, LIGHT SOURCE DEVICE, AND CONTROL METHOD FOR LIGHT SOURCE DEVICE

CROSS-REFERENCE TO RELATED APPLICATION

This application is based upon and claims the benefit of priority to PCT Application No. PCT/JP2019/018601, filed on May 9, 2019, the entire contents of which are incorporated herein by reference.

TECHNICAL FIELD

The embodiments discussed herein relate to an imaging system and an endoscope system that image a subject in a state where illumination light is irradiated.

BACKGROUND

An endoscope system is known as one of imaging systems capable of capturing an image of a narrow space or a closed space that is difficult for a person to directly observe, such as the inside of a human body. The endoscope system is provided with an imaging unit and an optical system for illumination at the tip of a flexible transmission path including an optical fiber and a conductive wire, and captures an image of the subject while the subject is irradiated with illumination light through the optical system.

One of this type of imaging systems has an imaging unit including a CMOS image sensor and a reading unit for reading an electric signal (video data) from the CMOS image sensor, and reads out an electric signal in a rolling shutter mode at the reading unit. When the electric signal is read in the rolling shutter mode, a light receiving surface of the CMOS image sensor is divided into a plurality of horizontal lines, and the electric signal is sequentially read out on a horizontal-line basis, so that the timing for reading out the electric signal is different among the horizontal lines. Therefore, when the subject is imaged under an environment having no external light (that is, under an environment where only illumination light emitted from the tip of the transmission path to the subject serves as a light source), a time of period (exposure period) for which the light is received is different among the horizontal lines in the CMOS image sensor, so that unevenness in brightness may occur in an image and thus image quality may deteriorate.

As one of techniques for reducing the unevenness in brightness caused by the difference in exposure time is known a method for adjusting the color balance of light of a plurality of colors emitted from a plurality of light emitting elements based on the light amounts of the light of the plurality of colors and controlling an exposure timing when a subject illuminated with the light of the plurality of colors on which the color balance has been adjusted is imaged.

SUMMARY

According to an aspect of the embodiment, an imaging system includes a light source for emitting illumination light with which a subject is irradiated; an image sensor in which pixels for generating electric signals by receiving light from the subject and performing photoelectric conversion on the received light are arranged two-dimensionally; a reading circuit for sequentially reading out the electrical signals on a horizontal-line basis from the light receiving unit; a lighting controller for independently controlling emission of illumination light to be emitted by the light source in: (i) a non-all-line exposure period, which contains a reading period in which electrical signals are sequentially read out on a horizontal-line basis from an image sensor for one frame or one field period, and in which at least one horizontal line of the horizontal lines for the one frame or the one field period is not exposed to light, and (ii) in an all-line exposure period, in which all of the horizontal lines for the one frame or the one field period are exposed to light.

The object and advantages of the embodiment will be realized and attained by means of the elements and combinations particularly pointed out in the claims.

It is to be understood that both the foregoing general description and the following detailed description are exemplary and explanatory and are not restrictive of the embodiment.

BRIEF DESCRIPTION OF DRAWINGS

FIG. 13 is a graph showing an example of a method of controlling the maximum light amount of illumination light to be emitted by a light source.

DESCRIPTION OF EMBODIMENTS

When electric signals for one frame or one field period are read out from an image sensor (CMOS image sensor) in a rolling shutter mode in the above-mentioned imaging system, a period in which at least one horizontal line is not exposed to light exists before and after an all-line exposure period in which all horizontal lines have been exposed to light. Therefore, the difference in the exposure period between two adjacent horizontal lines is large, so that remarkable unevenness in brightness (strips) may occur at the boundary portion between the two horizontal lines, resulting in deterioration of image quality.

Hereinafter, some embodiments that can prevent such deterioration in image quality in an imaging system for imaging a subject while the subject is irradiated with illumination light will be described with reference to the drawings.

Figure 1:
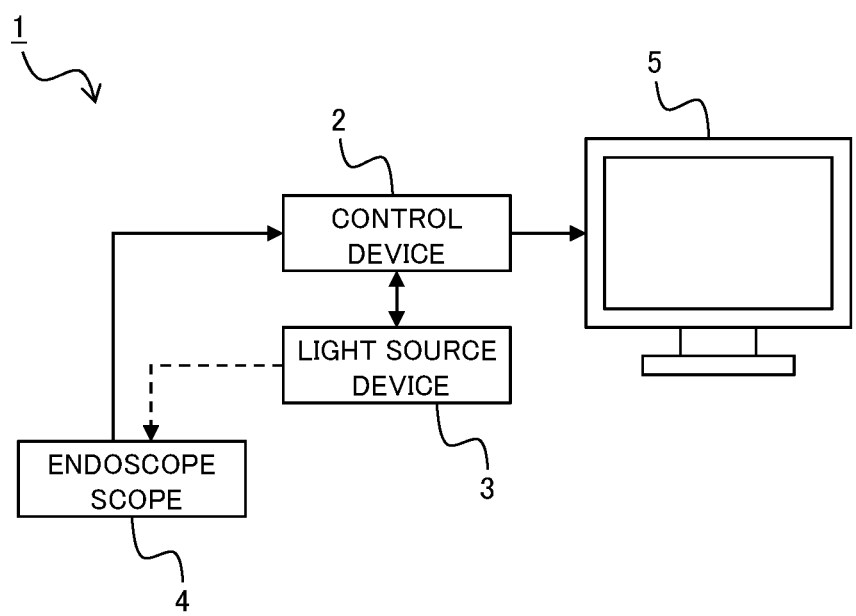
FIG. 1 is a diagram showing a system configuration example of an imaging system according to an exemplary embodiment.

FIG. 1 is a diagram showing a system configuration example of an imaging system according to an exemplary embodiment. FIG. 1 shows an example of a system configuration of an endoscope system which is an example of the imaging system 1 according to the present embodiment. In the following description, the imaging system 1 is also referred to as an endoscope system 1.

The imaging system 1 includes a control device 2, a light source device 3, an endoscope scope 4, and a display device 5. The control device 2 is a device for performing various processing containing processing of acquiring data of a video or an image (hereinafter collectively referred to as "video") captured by the endoscope scope 4 as an imaging device and displaying the video on the display device 5, and processing of controlling the light amount of illumination light to be provided to the endoscope scope 4. The control device 2 may be dedicated hardware, or may be a device for causing a general-purpose computer such as a personal computer to execute a control program described later. The light source device 3 is a device for emitting illumination light to illuminate a subject to be imaged by the endoscope scope 4 as an imaging device. The light source device 3 controls the light amount of illumination light to be emitted (illumination light amount) based on the control signal (control information) from the control device 2. The illumination light emitted by the light source device 3 is transmitted to a tip portion of the endoscope scope 4 through an optical transmission path such as an optical fiber of the endoscope scope 4, and emitted from the tip portion to an imaging range. The endoscope scope 4 is an imaging device capable of imaging a narrow space or a closed space that is difficult for a person to directly observe, such as the inside of a human body. The endoscope scope 4 is provided with a lighting unit (lighting system 42) and an imaging unit 41 at one end (tip portion) of a flexible transmission path. The display device 5 is, for example, a liquid crystal display.

Figure 2:
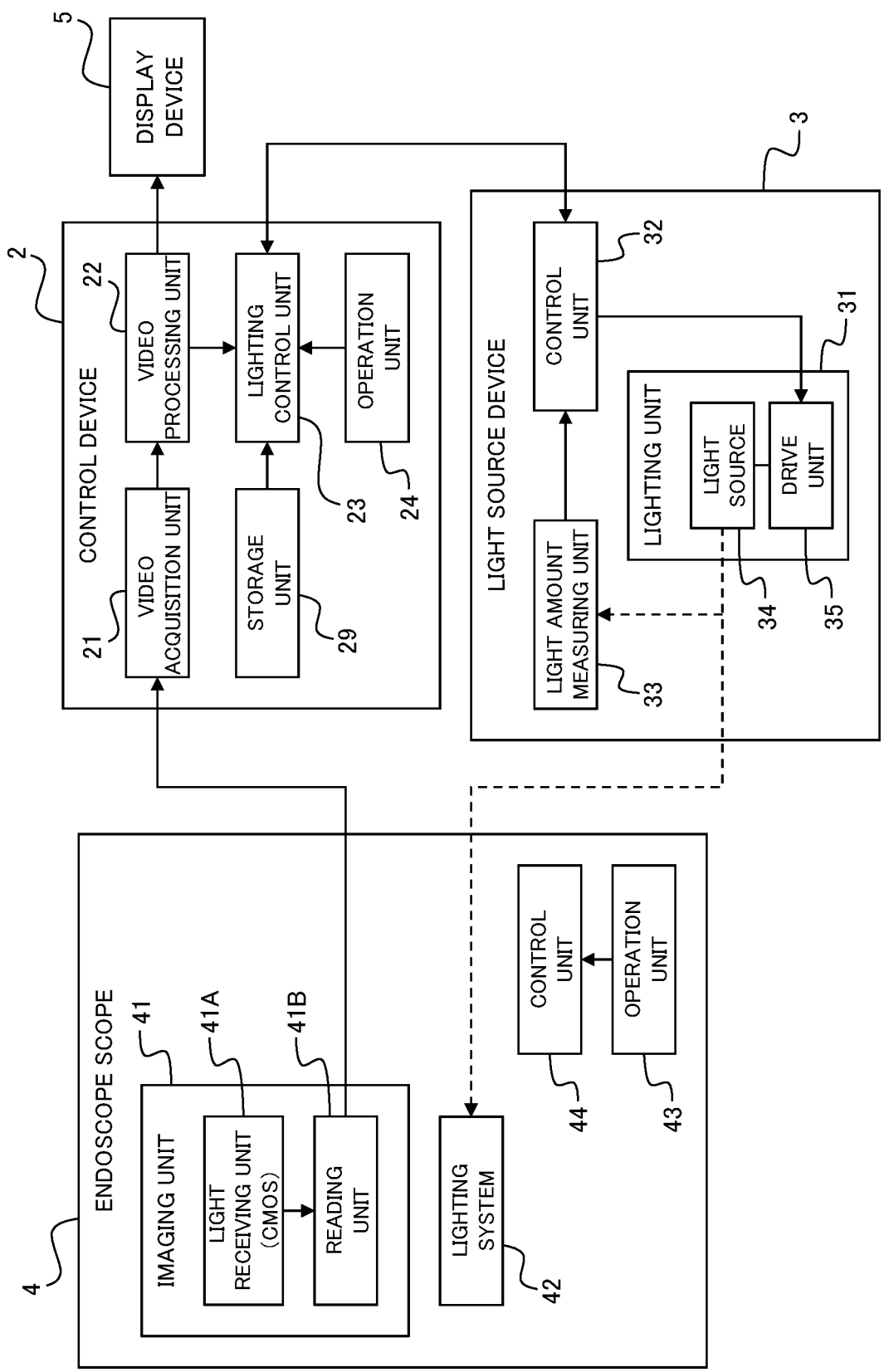
FIG. 2 is a diagram showing a functional block of the imaging system.
Figure 3:
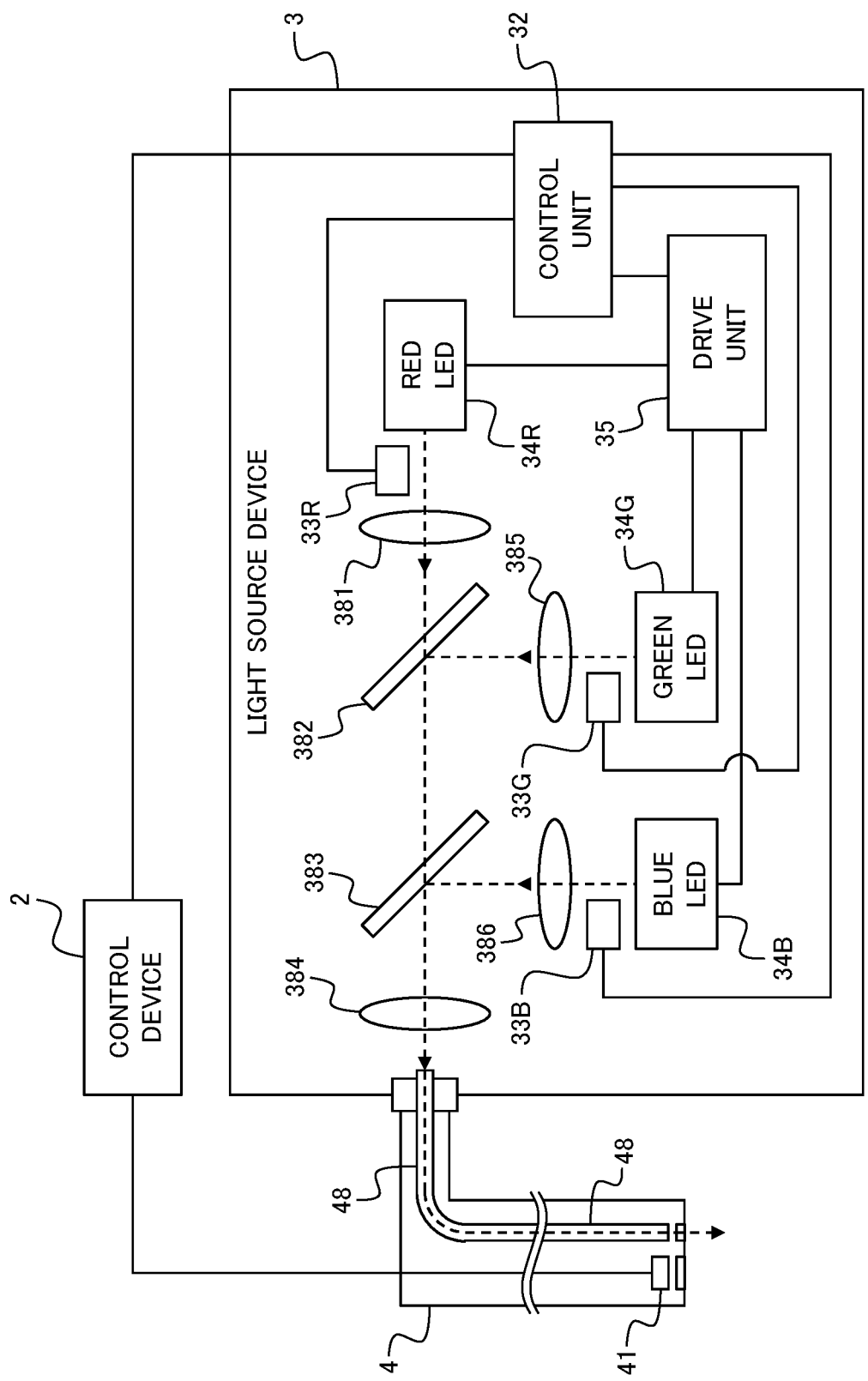
FIG. 3 is a diagram showing a configuration example of a light source device.

FIG. 2 is a diagram showing a functional block of the imaging system according to the present embodiment. FIG. 3 is a diagram showing a configuration example of the light source device. As shown in FIG. 2, the control device 2 of the imaging system 1 includes a video acquisition unit 21, a video processing unit 22, a lighting control unit 23, an operation unit 24, and a storage unit 29. Further, the light source device 3 of the imaging system 1 includes a lighting unit 31, a control unit 32, and a light amount measuring unit 33. Further, the endoscope scope 4 of the imaging system 1 includes an imaging unit 41, a lighting system 42, an operation unit 43, and a control unit 44.

The video acquisition unit 21 acquires an electric signal representing a video of a subject captured by the imaging unit 41 of the endoscope scope 4. The imaging unit 41 of the endoscope scope 4 includes a light receiving unit 41A and a reading unit 41B. The light receiving unit 41A is a light receiving element in which pixels for generating an electric signal by receiving light and performing photoelectric conversion on the received light are arranged two-dimensionally, and it is a CMOS image sensor in the present embodiment. The reading unit 41B reads out an electric signal generated by each pixel of the light receiving unit 41A, and transmits it to the control device 2. The reading unit 41B reads out the electric signal generated by each pixel of the light receiving unit 41A in a rolling shutter mode. The reading unit may be a reading circuit, which may or may not be integrated into the image sensor.

The video processing unit 22 performs predetermined processing on the electric signal representing the video of the subject acquired by the image acquisition unit 21, and causes the display device 5 to display the video of the subject thereon. The video processing unit 22 performs processing such as correction of distortion which is caused due to the reading of an electric signal in the rolling shutter mode, and correction of brightness (luminance) and color in the video of the subject image. Further, the video processing unit 22 transfers information representing the brightness of the video of the subject to the lighting control unit 23.

The lighting control unit 23 controls the light amount of illumination light to be emitted by the lighting unit 31 of the light source device 3 based on a set value of brightness (set light amount) of the illumination light which is input by a user operating the operation unit 24, and the light amount of illumination light for the subject. The lighting unit 31 includes a light source (for example, an LED) 34 capable of emitting pulses, and a drive unit 35 for applying a drive current to the light source 34. The light amount of illumination light for the subject is measured, for example, by the light amount measuring unit 33 of the light source device 3. As shown in FIG. 3, the light source device 3 in the imaging system 1 of the present embodiment includes three types of light sources having different emission light colors such as a red LED 34R, a green LED 34G, and a blue LED 34B as the light source 34, for example, and the subject is irradiated with white light obtained by mixing (mixing the colors of) the light emitted by these light sources as illumination light. The light amount measuring unit 33 measures each of the light amount of red light emitted by the red LED 34R, the light amount of green light emitted by the green LED 34G, and the light amount of blue light emitted by the blue LED 34B.

The lighting control unit 23 of the control device 2 according to the present embodiment variably controls the illumination light emitted by the lighting unit 31 in at least a part of a reading period (hereinafter, also referred to as "non-all-line exposure period") in which the reading unit 41B reads out the horizontal lines of the light receiving unit 41A for one frame or one field period, and also variably controls the illumination light emitted by the lighting unit 31 in at least a part of a non-reading period (hereinafter, also referred to as "all-line exposure period") other than the reading period. Further, the lighting control unit 23 of the control device 2 according to the present embodiment controls at least one of the pulse width and the number of pulses in a pulse current to be applied to the light source 34 (34R, 34G, 34B) of the lighting unit 31 based on the illumination light amount measured by the light amount measuring unit 33.

The operation unit 24 is used to accept various inputs to the control device 2 by the user, and includes, for example, a switch for adjusting the brightness (illumination light amount) of the illumination light to be applied to the subject. The storage unit 29 stores programs for causing the control device 2 and the like to perform predetermined operations, and various kinds of information. The storage unit 29 stores, for example, information indicating the corresponding relation between a set light amount and a method of applying a drive current to the light source 34 (34R, 34G, 34B).

As described above, the light source device 3 includes a lighting unit 31, a control unit 32, and a light amount measuring unit 33. The lighting unit 31 includes the light source 34 and the drive unit 35.

The light source 34 is a light emitting device such as an LED capable of emitting pulses, and emits light in a predetermined wavelength range fit for a subject to be imaged. In the present embodiment, as shown in FIG. 3, a combination of three types of light sources of a red LED 34R, a green LED 34G, and a blue LED 34B is used as the light source 34. Light emitted by the red LED 34R passes through a first lens 381, a first half mirror 382, a second half mirror 383, and a second lens 384 and enters a light guide 48 of the endoscope scope 4. Light emitted by the green LED 34G passes through a third lens 385, and is reflected by the first half mirror 382 in a direction in which the second half mirror 383 is arranged. The reflected light then passes through the second half mirror 383 and the second lens 384 and enters the light guide 48 of the endoscope scope 4. Light emitted by the blue LED 34B passes through a fourth lens 386 and is reflected by the second half mirror 383 in a direction in which the second lens 384 is arranged. The reflected light then passes through the second lens 384 and enters the light guide 48 of the endoscope scope 4. Therefore, the color of the illumination light to be applied to the subject through the light guide 48 can be controlled by adjusting the light amount of light emitted from each of the light sources of the red LED 34R, the green LED 34G, and the blue LED 34B. Note that the light source 34 of the lighting unit 31 is not limited to the combination of the above three types of light sources of the red LED 34R, the green LED 34G, and the blue LED 34B, and may be another combination or one type.

The drive unit 35 generates a drive current to be applied to the light source 34 (34R, 34G, 34B) based on the control signal (control information) from the control unit 32, and applies the drive current to the light source 34. The control unit 32 generates a control signal (control information) containing information indicating the value of the drive current to be applied to each of the red LED 34R, the green LED 34G, and the blue LED 34B based on the control signal (control information) from the lighting control unit 23 of the control device 2, and provides the control signal to the drive unit 35.

The light amount measuring unit 33 measures the light amount of the illumination light which is emitted from the lighting unit 31 and transmitted to the endoscope scope 4. When the light source 34 includes the three types of light sources of the red LED 34R, the green LED 34G, and the blue LED 34B, the light amount measuring unit 33 includes, for example, a first optical sensor 33R, a second optical sensor 33G and a third optical sensor 33B as shown in FIG. 3. Each of the first optical sensor 33R, the second optical sensor 33G, and the third optical sensor 33B is, for example, an optical sensor having an electronic shutter function, and can change the exposure period for detecting the light amount of light according to the setting of the control unit 32. The first optical sensor 33R is used to measure the light amount of red light emitted by the red LED 34R. The second optical sensor 33G is used to measure the light amount of green light emitted by the green LED 34G. The third optical sensor 33B is used to measure the light amount of blue light emitted by the blue LED 34B. A measurement result of the illumination light amount by the light amount measuring unit 33 (the first optical sensor 33R, the second optical sensor 33G, and the third optical sensor 33B) is notified to, for example, the lighting control unit 23 of the control device 2 via the control unit 32 of the light source device 3.

As described above, the endoscope scope 4 includes the imaging unit 41, the lighting system 42, the operation unit 43, and the control unit 44. The imaging unit 41 includes the light receiving unit 41A in which pixels for generating an electric signal by receiving light and performing photoelectric conversion on the received light are arranged two-dimensionally, and the reading unit 41B for reading out the electrical signal generated by each pixel of the light receiving unit 41A in the rolling shutter mode. The lighting system 42 includes an optical system such as a lens for causing illumination light emitted from the light source device 3 and transmitted to the tip portion through the transmission path such as the light guide 48 (see FIG. 3) to be emitted to a spatial region corresponding to a predetermined imaging range (angle of view). The operation unit 43 is used to accept various inputs to the endoscope scope 4 by the user, and includes, for example, an operation lever or the like for changing an imaging direction and an emission direction of the illumination light. The control unit 44 controls the operation of the endoscope scope 4 based on operation information and the like input from the operation unit 43.

As described above, the imaging unit 41 in the imaging system 1 of the present embodiment reads out the electric signal generated by each pixel (sensor) of the light receiving unit 41A in the rolling shutter mode. In other words, the reading unit 41B sequentially reads out electric signals generated from a plurality of pixels arranged two-dimensionally on a set (line) basis, each set (line) including a plurality of pixels arranged in one direction.

Figure 4:
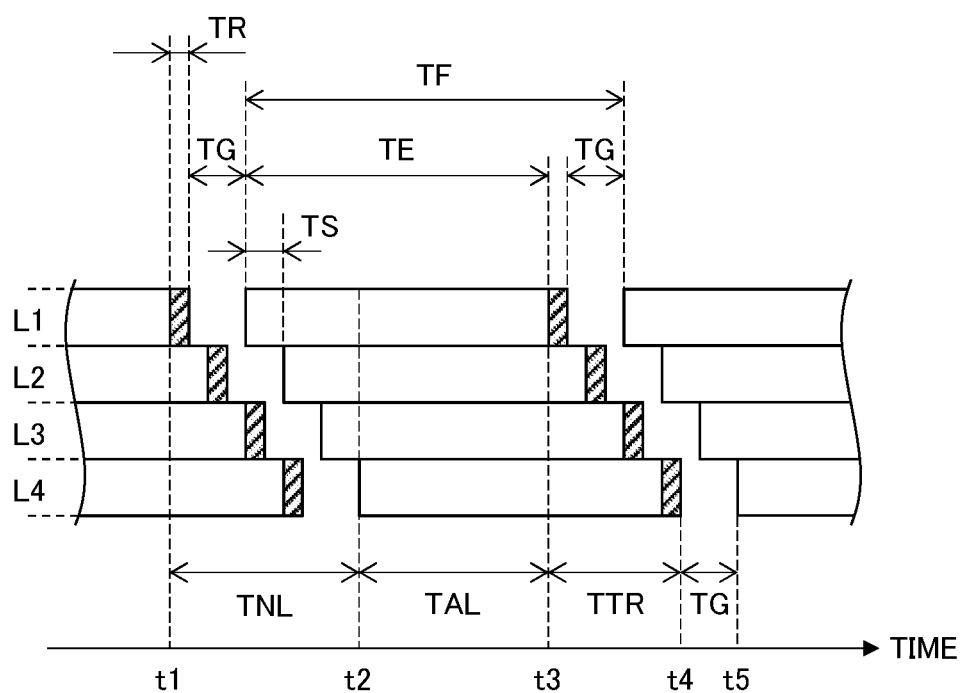
FIG. 4 is a diagram showing a video reading method of a rolling shutter mode.

FIG. 4 is a diagram showing a video reading method based on the rolling shutter mode. For the sake of simplicity of description, FIG. 4 shows an exposure period and a reading period for each of four horizontal lines L1 to L4 when one frame of a video is divided into the four horizontal lines L1 to L4 to read electric signals.

A time TF required to read electric signals for one frame in the video from one line (for example, the first line L1 in FIG. 4) is equal to the sum of an exposure period TE for the one line, a line reading period TR, and a reset period TG (that is, TF=TE+TR+TG). The exposure period TE is a period in which pixels in a line to be exposed to light are caused to receive light and generate electric signals through photoelectric conversion. The line reading period TR is a period in which the electrical signal generated through photoelectric conversion by each pixel in the line to be exposed to light is read out. The reset period TG is a period in which information remaining in each pixel (for example, residual charge) is removed.

Further, in the rolling shutter mode, when reading electric signals for one frame of a video, respective exposure start times for the four lines L1 to L4 are shifted from one another so that the respective exposure times are different from one another. In the example shown in FIG. 4, when reading the electric signals for one frame of the video, exposure is started from the uppermost line L1 among the four lines L1 to L4, and subsequently, exposure is started from a line which is located below the line L1 and closest to the line L1 (that is, in the order of line L2, line L3, and line L4). At this time, the time difference TS between the exposure start time for certain one line and the exposure start time for a line on which exposure is performed next to the certain one line is not required to be longer than the line reading period TR as shown in FIG. 4, and for example, TS=TR or the like may be set.

As described above, in the rolling shutter mode, the start and end times of the exposure period TE are different among lines each of which is a set of pixels when information (electric signals) of pixels is read out. Therefore, a period from a time t1 at which the reading of the electric signal of the first line L1 for certain one frame is started until an exposure start time t2 for the fourth line L4 for a next frame is a period in which at least one line has not been exposed to light. In the following description, the period TNL in which at least one line has not been exposed to light is referred to as "non-all-line exposure period TNL". As shown in FIG. 4, the non-all-line exposure period TNL includes a frame reading period TTR from a time t3 at which the reading of the electric signal of an initial line (first line L1) for certain one frame is started until a time t4 at which the reading of the electric signal of a last line (fourth line L4) for the certain one frame is ended, and a period from the time t4 until an exposure start time t5 of the last line (fourth line L4) for a next frame (that is, the reset period TG). Therefore, in the following description, the non-all-line exposure period TNL is also referred to as reading period TNL.

Further, in the following description, a period TAL in which all lines have been exposed to light like the period from the time t2 to the time t3 is referred to as all-line exposure period TAL. The all-line exposure period TAL does not include the line reading period TR. Therefore, in the following description, the all-line exposure period TAL is also referred to as non-reading period TAL.

When reading the electric signal of each pixel in the rolling shutter mode, a period required to read electric signals for one frame or one field is in the order of the non-all-line exposure period TNL, the all-line exposure period TAL, and the non-all-line exposure period TNL.

Figure 5:
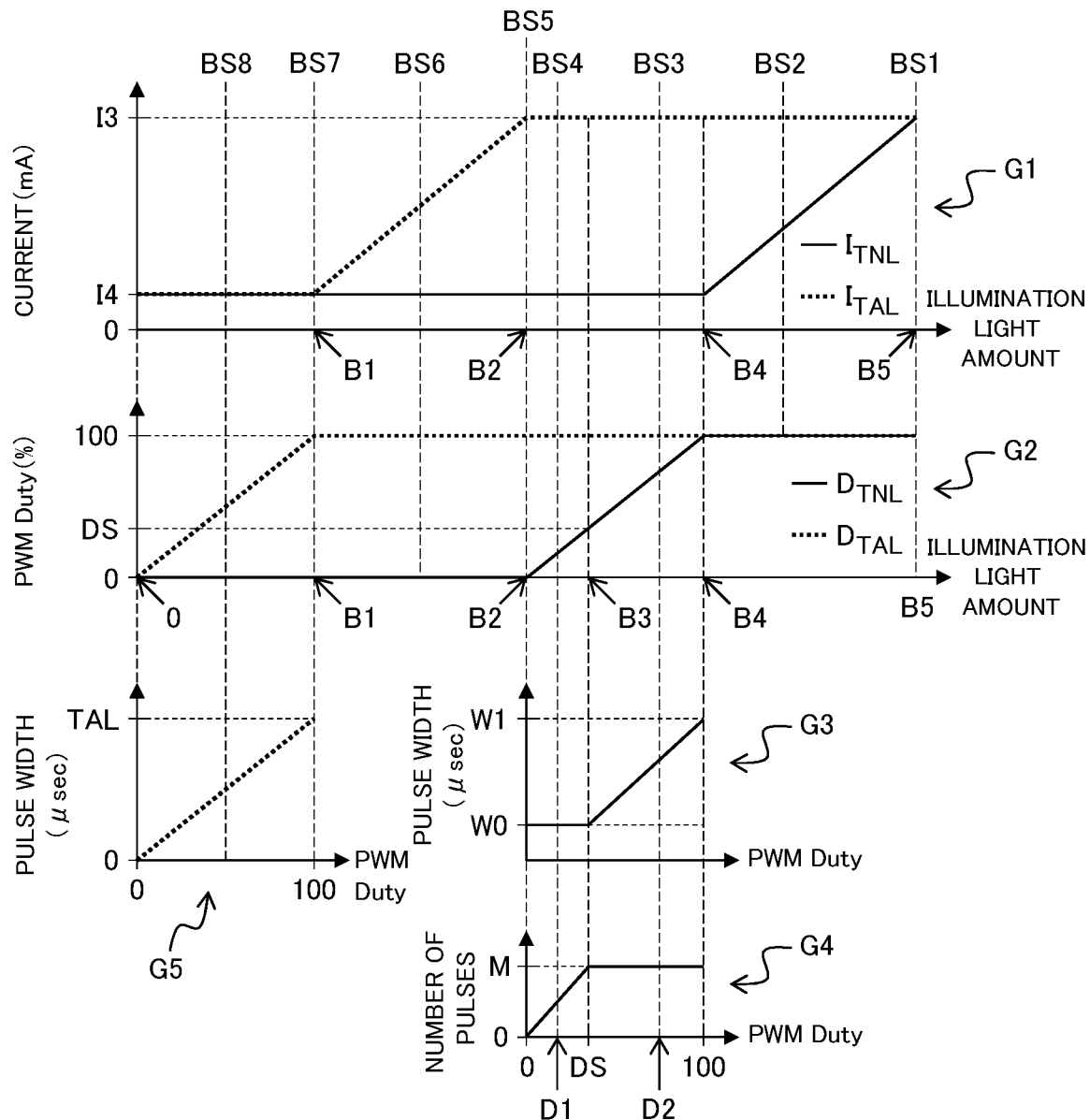
FIG. 5 is a graph showing a method of controlling the amount of illumination light.

FIG. 5 is a graph showing a method of controlling the illumination light amount according to the present embodiment.

A graph G1 of the current vs. illumination light amount shown in an uppermost part of FIG. 5 illustrates the relation between the set value (set light amount) of the illumination light amount set by the user or the control device 2 or the like and the current to be applied to one of the light sources included in the light source 34 (for example, the red LED 34R). In the following description, one of the light sources included in the light source 34 is simply referred to as "light source 34". In the graph G1, a relation $I_{TNL}$ indicated by a solid line shows the relation between the drive current to be applied to the light source 34 during the non-all-line exposure period (reading period) TNL and the illumination light amount. In the graph G1, a relation $I_{TAL}$ indicated by a dotted line shows the relation between the drive current to be applied to the light source 34 during the all-line exposure period (non-reading period) TAL and the illumination light amount.

In the relation $I_{TAL}$ shown in the graph G1, the current value for the set light amount in the range of a light amount 0 as a minimum value to a first light amount B1 is equal to a minimum current value I4. Based on the rating of the light source 34, the minimum current value I4 is set within a current value range in which the light source 34 emits light (lights up). For example, the minimum current value I4 is set to be equal to or greater than a lower limit current value at which the drive unit 35 can drive the light source 34, or set to be equal to or greater than a minimum current value at which the light emission of the light source 34 is ensured. Further, in the relation $I_{TAL}$ shown in the graph G1, the current value for the set light amount in the range of a second light amount B2 larger than the first light amount B1 to a maximum light amount B5 which is further larger than the second light amount B2 is equal to a maximum current value I3. Based on the rating of the light source 34, the maximum current value I3 is set to a predetermined value equal to or less than a current value at which the light amount of light emitted from the light source 34 is maximum. Further, in the relation $I_{TAL}$ shown in the graph G1, the current value for the set light amount in the range of the first light amount B1 to the second light amount B2 is proportional to the set light amount in the range of the minimum current value I4 to the maximum current value I3. In other words, when the set light amount is in the range of the first light amount B1 to the second light amount B2, the current value is closer to the maximum current value I3 as the set light amount is closer to the second light amount B2.

On the other hand, in the relation $I_{TNL}$ shown in the graph G1, the current value for the set light amount in the range of the light amount 0 to a fourth light amount B4 which is larger than the second light amount B2 and smaller than the maximum light amount B5 is equal to the minimum current value I4. The fourth light amount B4 is further larger than a third light amount B3 which is larger than the second light amount B2. The third light amount B3 is a light amount serving as a threshold value to be used to determine which one of the control of applying a current having a constant current value over the entire non-all-line exposure period TNL and the pulse width modulation (PWM) control should be used to control the current in the non-all-line exposure period TNL. Further, in the relation $I_{TNL}$ shown in the graph G1, the current value for the set light amount in the range of the fourth light amount B4 to the maximum light amount B5 is proportional to the set light amount in the range of the minimum current value I4 to the maximum current value I3. In other words, when the set light amount is in the range of the fourth light amount B4 to the maximum light amount B5, the current value is closer to the maximum current value I3 as the set light amount is closer to the maximum light amount B5.

Note that in the imaging system 1 of the present embodiment, the current value to be applied to the light source 34 is determined based on the relation $I_{TNL}$ and the relation $I_{TAL}$ shown in the graph G1, and a method of applying the drive current (pulse current) is determined based on a graph G2 of PWM Duty vs. illumination light amount shown below the graph G1.

The graph G2 illustrates the relation between the set light amount and the duty ratio in PWM control (that is, the percentage of a value obtained by dividing the width of one pulse by the cycle). In the present embodiment, the period corresponding to the cycle of the PWM control is the non-all-line exposure period TNL and the all-line exposure period TAL. A relation $D_{TNL}$ indicated by a solid line in the graph G2 shows the relation between the set light amount and the duty ratio for the drive current to be applied to the light source 34 during the non-all-line exposure period (reading period) TNL. A relation $D_{TAL}$ indicated by a dotted line in the graph 2G shows the relation between the set light amount and the duty ratio for the drive current to be applied to the light source 34 during the all-line exposure period (non-reading period) TAL. Note that the duty ratio becomes equal to 100% when the width of one pulse matches the cycle. In other words, when the duty ratio of a target period (any one or both of the non-all-line exposure period TNL and the all-line exposure period TAL) is equal to 100%, one pulse current having a current value determined based on the graph G1 is applied over the entire target period. Therefore, when the duty ratio is equal to 100%, the lighting control unit 23 of the control device 2 performs current control for controlling the current value to be applied over the entire target period.

In the relation $D_{TAL}$ indicated by the dotted line in the graph G2, the duty ratio for the set light amount in the range of the first light amount B1 to the maximum light amount B5 is equal to 100%. Further, in the relation $D_{TAL}$ shown in the graph G2, the duty ratio for the set light amount in the range of the light amount 0 to the first light amount B1 is proportional to the set light amount in the range of 0% to 100%. In other words, when the set light amount is in the range of the light amount 0 to the first light amount B1, the value of the duty ratio is larger and approaches to 100% as the set light amount is closer to the first light amount B1. Therefore, when the set light amount is from the first light amount B1 to the maximum light amount B5, the lighting control unit 23 controls the drive current to be applied to the light source 34 during the all-line exposure period TAL according to the control method of applying a constant current over the all-line exposure period TAL. In other words, the lighting control unit 23 sets, as the current to be applied, a pulse current of one pulse which has a current value determined based on the set light amount and the relation $I_{TAL}$ in the graph G1 and has a pulse width matching the all-line exposure period TAL.

On the other hand, when the set light amount is in the range of the light amount 0 to the first light amount B1, the lighting control unit 23 controls the drive current to be applied to the light source 34 during the all-line exposure period TAL according to the PWM control. Specifically, the lighting control unit 23 sets, as the drive current to be applied to the light source 34 during the all-line exposure period TAL, a pulse current of one pulse which has the minimum current value I4 and whose pulse width is a period calculated based on the all-line exposure period TAL and the duty ratio corresponding to the magnitude of the set light amount. The pulse width is set to, for example, a pulse width which is equal to 0 μsec at the light amount 0, equal to the all-line exposure period TAL at the first light amount B1, and proportional to the set light amount as shown in a graph 5 below the section from the light amount 0 to the first light amount B1 in the graph G2.

On the other hand, in the relation $D_{TNL}$ shown in the graph G2, the duty ratio for the set light amount in the range of the light amount 0 to the second light amount B2 is equal to 0%. Therefore, when the set light amount is in the range of 0 to the second light amount B2, the lighting control unit 23 applies no drive current to the light source 34 during the non-all-line exposure period TNL. Further, in the relation $D_{TNL}$ shown in the graph G2, the duty ratio for the set light amount in the range of the fourth light amount B4 to the maximum light amount B5 is equal to 100%. Therefore, when the set light amount is in the range of the fourth light amount B4 to the maximum light amount B5, the lighting control unit 23 controls the drive current to be applied to the light source 34 during the non-all-line exposure period TNL according to the control method of applying a constant current over the entire non-all-line exposure period TNL. In other words, the lighting control unit 23 sets a pulse current of one pulse which has the current value determined based on the set light amount and the relation $I_{TNL}$ of the graph G1 and has a pulse width matching the non-all-line exposure period TNL.

Further, in the relation DTNL shown in the graph G2, the duty ratio for the set light amount in the range of the second light amount B2 to the fourth light amount B4 is proportional to the set light amount in the range of 0% to 100%. Therefore, when the set light amount is in the range of the second light amount B2 to the fourth light amount B4, the lighting control unit 23 controls the drive current to be applied to the light source 34 during the non-all-line exposure period TNL according to the PWM control. Specifically, the lighting control unit 23 sets, as the drive current to be applied to the light source 34 during the non-all-line exposure period TNL, a pulse current of a plurality of pulses which is obtained by dividing a period calculated based on the non-all-line exposure period TNL and the duty ratio corresponding to the magnitude of the set light amount into a plurality of periods and defining one period of the plurality of divided periods as a pulse width. The current value of each pulse in the pulse current of the plurality of pulses is set to the minimum current value I4. When the pulse current of the plurality of pulses is applied to the non-all-line exposure period TNL, for example, as shown in two graphs G3 and G4 drawn below the section from the second light amount B2 to the fourth light amount B4 in the graph G2, the minimum value of the pulse width per pulse and the maximum value of the number of pulses in a pulse current to be applied are set in advance, and the pulse current is generated based on these settings. The minimum value W0 of the pulse width per pulse is set based on, for example, the minimum value of the pulse width which enables the light source 34 to emit a light pulse and the shortest time during which the output and non-output of current in the drive unit 35 can be switched to each other. The minimum value of the pulse width per pulse is set to, for example, about 16.6 μsec. The maximum value of the number of pulses is set in a range where the product of the minimum value W0 of the pulse width and the maximum value M of the number of pulses is neither equal to nor more than the non-all-line exposure period TNL, and also in a range where individual light pulses are not continuously emitted when the set light amount is in a vicinity of the fourth light amount B4.

Further, when the drive current to be applied during the non-all-line exposure period TNL is PWM-controlled, the control based on the pulse width and the control based on the number of pulses are switched to each other with the third light amount B3 between the second light amount B2 and the fourth light amount B4 being defined as a boundary as illustrated in the graphs G3 and G4 of FIG. 5. When the set light amount is in the range of the third light amount B3 to the fourth light amount B4, the lighting control unit 23 increases or decreases the pulse width according to the magnitude of the set light amount with the number of pulses being set to a maximum value M. When the set light amount is in the range of the second light amount B2 to the third light amount B3, the lighting control unit 23 increases or decreases the number of pulses according to the magnitude of the set light amount with the pulse width being set to the minimum value W0.

Figure 6:
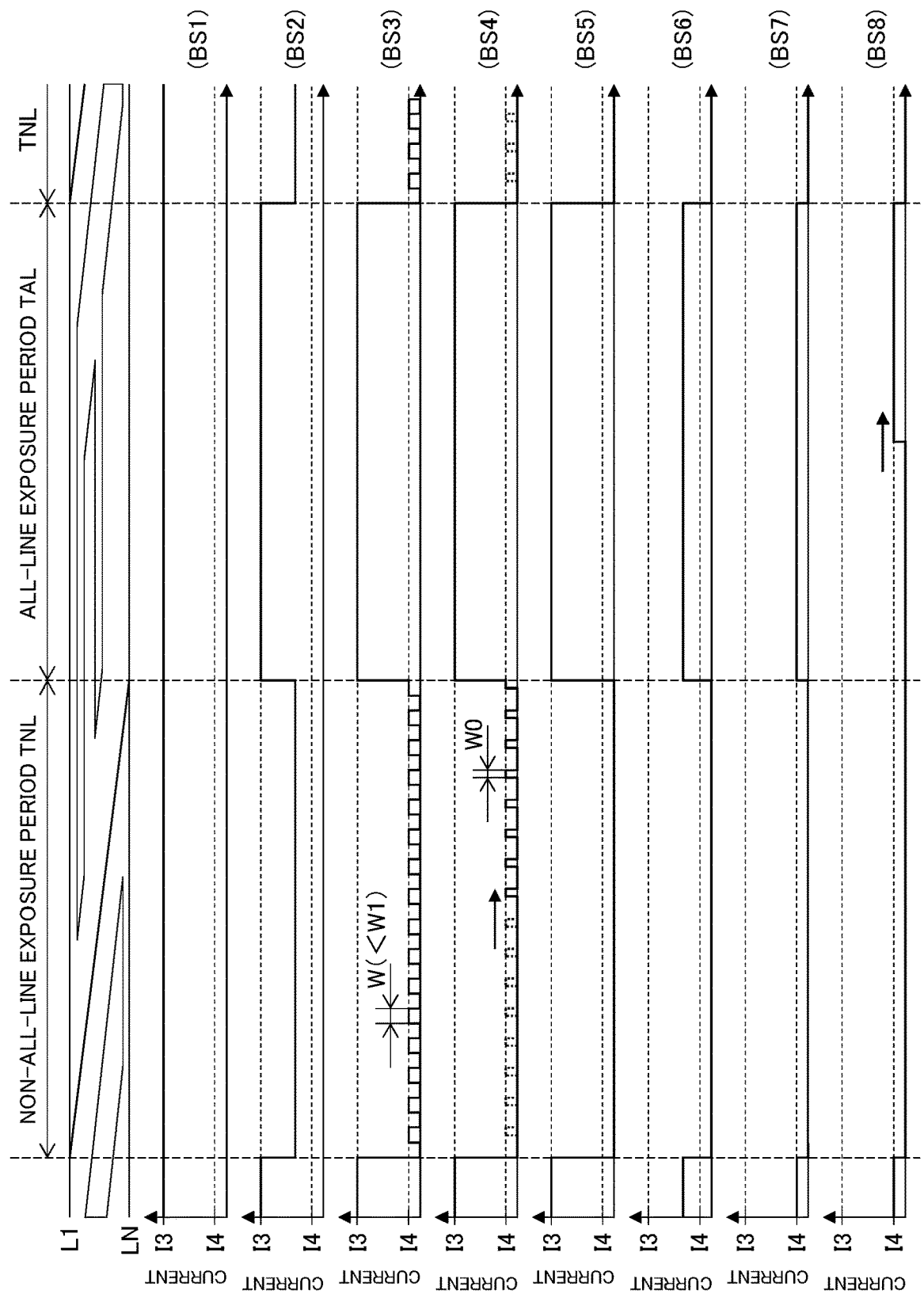
FIG. 6 is a graph showing the relation between the amount of illumination light and a current applying method.

FIG. 6 is a graph showing the relation between the illumination light amount and the current applying method according to the present embodiment. Note that FIG. 6 shows an example of the drive current to be applied to the light source 34 when each of set light amounts BS1 to BS8 shown in the graph of FIG. 5 is set. Here, each of the set light amounts BS1 to BS8 may be an illumination light amount which is set by a method of operating the operation unit 24 of the control device 2 by the user of the imaging system 1, or may be an illumination light amount measured by the light amount measuring unit 33 or an illumination light amount set by the lighting control unit 23 based on the brightness (luminance) or the like of a video notified from the image processing unit 22.

The set light amount BS1 is the maximum light amount B5, and both the duty ratios of the PWM control for the drive currents to be applied during the non-all-line exposure period TNL and during the all-line exposure period TAL are equal to 100%. Therefore, as shown in FIG. 6, in the case of the set light amount BS1, the lighting control unit 23 sets, as the drive currents to be applied to the light source 34 during the non-all-line exposure period TNL and during the all-line exposure period TAL, a current which has the maximum current value I3 and is to be applied over the entire period of each of TNL and TAL (a pulse current of one pulse whose pulse width matches each period).

The set light amount BS2 is smaller than the maximum light amount B5 and larger than the fourth light amount B4. Therefore, both the duty ratios of the PWM control for the drive currents to be applied during the non-all-line exposure period TNL and during the all-line exposure period TAL are equal to 100%. In the case of the set light amount BS2, the value of the drive current to be applied during the all-line exposure period TAL is the maximum current value I3. On the other hand, the value of the drive current to be applied during the non-all-line exposure period TNL is a value which is smaller than the maximum current value I3 and larger than the minimum current value I4. Therefore, as shown in FIG. 6, in the case of the set light amount BS2, the lighting control unit 23 sets, as the drive current to be applied to the light source 34 during the non-all-line exposure period TNL, a current which has a current value corresponding to the set light amount BS2 and is to be applied over the entire non-all-line exposure period TNL. Further, the lighting control unit 23 sets, as the drive current to be applied to the light source 34 during the all-line exposure period TAL, a current which has the maximum current value I3 and is to be applied over the entire all-line exposure period TAL.

The set light amount BS3 is smaller than the fourth light amount B4 and larger than the third light amount B3. Therefore, the duty ratio of PWM control for the drive current to be applied during the all-line exposure period TAL is equal to 100%. On the other hand, the duty ratio of PWM control for the drive current to be applied during the non-all-line exposure period TNL is smaller than 100% and larger than the threshold DS. Further, the value of the drive current to be applied during the all-line exposure period TAL is the maximum current value I3, whereas the value of the drive current to be applied during the non-all line exposure period TNL is the minimum current value I4. Therefore, as shown in FIG. 6, in the case of the set light amount BS3, the lighting control unit 23 sets, as the drive current to be applied to the light source 34 during the non-all-line exposure period TNL, a pulse current of a plurality of pulses in which the number of pulses is a maximum value and a pulse width per pulse is a pulse width W corresponding to the set light amount BS3. The current value of each pulse in this pulse current is the minimum current value I4. Further, the lighting control unit 23 sets, as the drive current to be applied to the light source 34 during the all-line exposure period TAL, a current which has the maximum current value I3 and is to be applied over the entire all-line exposure period TAL.

Further, when the set light amount is larger than the set light amount BS3 and smaller than the fourth light amount B4, the pulse current to be applied during the non-all-line exposure period TNL is a pulse current which has the same number of pulses as the pulse current shown in FIG. 6 and in which the pulse width of one pulse is larger than W. Further, when the set light amount is smaller than the set light amount BS3 and larger than the third light amount B3, the pulse current to be applied during the non-all-line exposure period TNL is a pulse current which has the same number of pulses as the pulse current shown in FIG. 6 and in which the pulse width of one pulse is smaller than W.

The set light amount BS4 is smaller than the third light amount B3 and larger than the second light amount B2. Therefore, the duty ratio of PWM control for the drive current to be applied during the all-line exposure period TAL is equal to 100%. On the other hand, the duty ratio of PWM control for the drive current to be applied during the non-all-line exposure period TNL is smaller than the threshold DS and larger than 0%. Further, the value of the drive current to be applied during the all-line exposure period TAL is the maximum current value I3, whereas the value of the drive current to be applied during the non-all-line exposure period TNL is the minimum current value I4. Therefore, as shown in FIG. 6, in the case of the set light amount BS4, the lighting control unit 23 sets, as the drive current to be applied to the light source 34 during the non-all-line exposure period TNL, a pulse current in which the pulse width per pulse is the minimum width, and the number of pulses is a number corresponding to the set light amount BS4. The current value of each pulse in this pulse current is the minimum current value I4. Further, the lighting control unit 23 sets, as the drive current to be applied to the light source 34 during the all-line exposure period TAL, a current which has the maximum current value I3 and is to be applied over the entire all-line exposure period TAL.

Further, when the set light amount is larger than the set light amount BS4 and smaller than the third light amount BS3, the pulse current to be applied during the non-all-line exposure period TNL is a pulse current which has the same pulse width (minimum value W0) as the pulse current shown in FIG. 6 and has a large number of pulses. Further, when the set light amount is smaller than the set light amount BS4 and larger than the second light amount BS2, the pulse current to be applied during the non-all-line exposure period TNL is a pulse current which has the same pulse width (minimum value W0) as the pulse current shown in FIG. 6 and has a small number of pulses.

The set light amount BS5 is the second light amount B2. Therefore, the duty ratio of PWM control for the drive current to be applied during the all-line exposure period TAL is equal to 100%, whereas the duty ratio of PWM control for the drive current to be applied during the non-all-line exposure period TNL is equal to 0%. Further, the value of the drive current to be applied during the all-line exposure period TAL is the maximum current value I3, whereas the value of the drive current to be applied during the non-all-line exposure period TNL is the minimum current value I4. Therefore, as shown in FIG. 6, in the case of the set light amount BS5, the lighting control unit 23 determines that a pulse current in which the pulse width per pulse is the minimum width and the number of pulses is equal to 0 is applied to the light source 34 during the non-all-line exposure period TNL (that is, no drive current is applied to the light source 34 during the non-all-line exposure period TNL). Further, the lighting control unit 23 sets, as the drive current to be applied to the light source 34 during the all-line exposure period TAL, a current which has the maximum current value I3 and is to be applied over the entire all-line exposure period TAL.

The set light amount BS6 is smaller than the second light amount B2 and larger than the first light amount B1. In the case of the set light amount BS6, the duty ratio of PWM control for the drive current to be applied during the non-all-line exposure period TNL is equal to 0%. Therefore, as shown in FIG. 6, in the case of the set light amount BS6, the lighting control unit 23 determines that no drive current is applied to the light source 34 during the non-all-line exposure period TNL. In the case of the set light amount BS6, the duty ratio of PWM control for the drive current to be applied during the all-line exposure period TAL is still equal to 100%. However, the current value of the corresponding drive current is a value which is smaller than the maximum current value I3 and larger than the minimum current value I4. Therefore, as shown in FIG. 6, in the case of the set light amount BS6, the lighting control unit 23 sets, as the drive current to be applied to the light source 34 during the all-line exposure period TAL, a current which has a current value corresponding to the set light amount BS6 (a current value smaller than the maximum current value I3 and larger than the minimum current value I4) and is to be applied over the entire all-line exposure period TAL.

The set light amount BS7 is the first light amount B1. In the case of the set light amount BS7, the duty ratio of PWM control for the drive current to be applied during the non-all-line exposure period TNL is equal to 0%. Therefore, as shown in FIG. 6, in the case of the set light amount BS7, the lighting control unit 23 determines that no drive current is applied to the light source 34 during the non-all-line exposure period TNL. In the case of the set light amount BS7, the duty ratio of PWM control for the drive current to be applied during the all-line exposure period TAL is still equal to 100%. However, the current value of the corresponding drive current is the minimum current value I4. Therefore, as shown in FIG. 6, in the case of the set light amount BS7, the lighting control unit 23 sets, as the drive current to be applied to the light source 34 during the all-line exposure period TAL, a current which has the minimum current value I4 and is to be applied over the entire all-line exposure period TAL.

The set light amount BS8 is smaller than the first light amount B1 and larger than the light amount 0. In the case of the set light amount BS8, the duty ratio of PWM control for the drive current to be applied during the non-all-line exposure period TNL is equal to 0%. Therefore, as shown in FIG. 6, in the case of the set light amount BS8, the lighting control unit 23 determines that no drive current is applied to the light source 34 during the non-all-line exposure period TNL. Further, in the case of the set light amount BS8, the duty ratio of PWM control for the drive current to be applied during the all-line exposure period TAL is smaller than 100% and larger than 0%. Further, the current value of the drive current corresponding to the set light amount BS8 is the minimum current value I4. Therefore, as shown in FIG. 6, in the case of the set light amount BS8, the lighting control unit 23 sets, as the drive current to be applied to the light source 34 during the all-line exposure period TAL, a pulse current which is one pulse and has a pulse width determined based on the all-line exposure period TAL and the duty ratio. The current value of one pulse in this pulse current is the minimum current value I4.

As described above, the imaging system 1 of the present embodiment includes the lighting control unit 23 which can variably control the drive current to be applied to the light source 34 (that is, the illumination light emitted by the lighting unit 31) in at least a part of the non-all-line exposure period TNL containing the reading period TTR when the drive current is applied to the light source 34 based on the set light amount. Further, the lighting control unit 23 in the imaging system 1 of the present embodiment can also variably control the drive current to be applied to the light source 34 (that is, illumination light emitted by the lighting unit 31) in at least a part of the all-line exposure period TAL other than the non-all-line exposure period TNL. Further, the lighting control unit 23 in the imaging system 1 of the present embodiment can control the pulse width and the number of pulses in the pulse current to be applied to the light source 34 based on the illumination light amount measured by the light amount measuring unit 33, for example.

Figure 7:
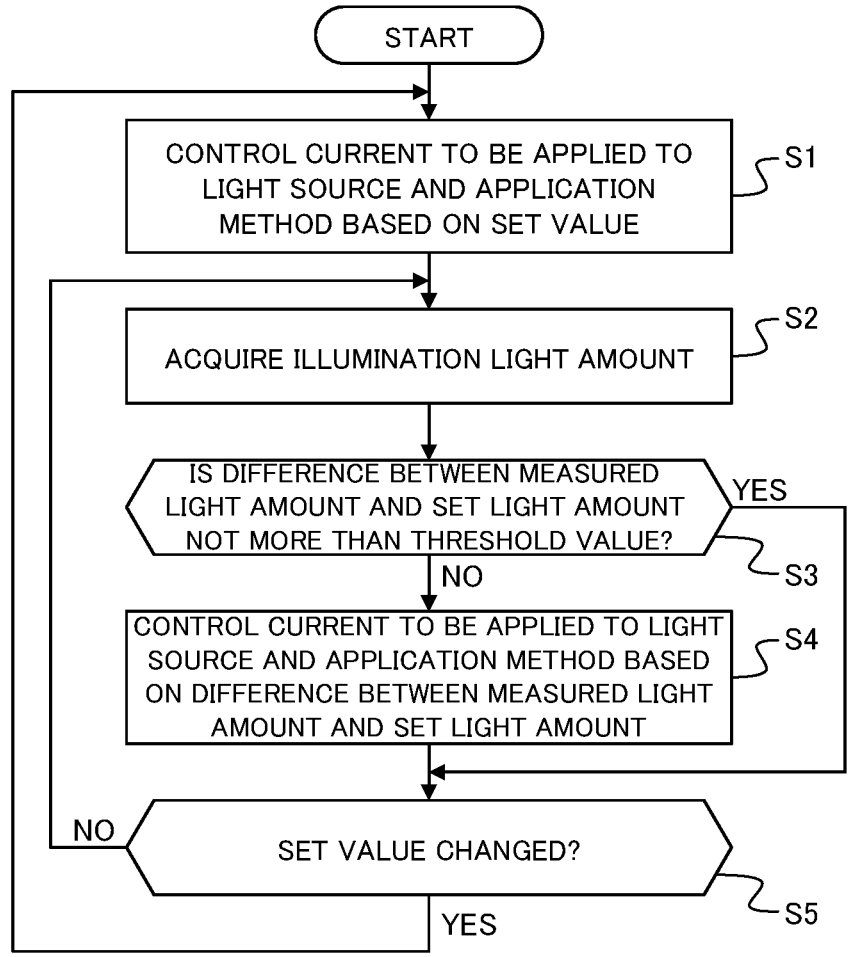
FIG. 7 is a flowchart showing an example of processing to be performed by the imaging system.

FIG. 7 is a flowchart illustrating an example of processing to be performed by the imaging system according to the present embodiment. FIG. 7 shows the processing which is performed by the control device 2 to control the pulse width and the number of pulses in the pulse current to be applied to the light source 34 as an example of the processing to be performed by the imaging system 1 of the present embodiment.

First, the control device 2 controls the current to be applied to the light source and the application method based on set values (step S1). The processing of step S1 is performed by the lighting control unit 23. The lighting control unit 23 controls the current value, pulse width, number of pulses, etc. of a drive current to be applied to the light source 34, for example, based on a set value of the illumination light amount set by the user of the imaging system 1 and control information of the illumination light amount as shown in FIG. 5. The lighting control unit 23 transmits control information such as the current value, the pulse width, and the number of pulses to the control unit 32 of the light source device 3. The control unit 32 of the light source device 3 operates the lighting unit 31 based on the received control information, and transmits illumination light emitted from the lighting unit 31 to the endoscope 4. When the light source 34 in the light source device 3 includes the red LED 34R, the green LED 34G, and the blue LED 34B as shown in FIG. 3, the lighting control unit 23 controls the current value, pulse width, number of pulses, etc. of a drive current to be applied to each of the LEDs 34R, 34G, and 34B.

Next, the control device 2 acquires the light amount of illumination light (illumination light amount) emitted by the light source 34 of the light source device 3 from the light source device 3 (step S2). The processing of step S2 is performed, for example, by the lighting control unit 23. The light source device 3 measures the light amount of illumination light emitted from the light source 34 by the light amount measuring unit 33, and transmits a measurement result to the control device 2 through the control unit 32.

Next, the control device 2 compares the light amount of illumination light measured by the light source device 3 with a light amount (set light amount) set in the control device 2, and determines whether the difference between them is equal to or less than a threshold value (step S3). When the difference between the illumination light amount and the set light amount is larger than the threshold value (step S3; NO), the control device 2 controls the current to be applied to the light source and the application method based on the difference between the measured light amount and the set light amount (step S4). The processing of step S4 is performed, for example, by the lighting control unit 23. For example, based on the control information of the illumination light amount as shown in FIG. 5, the lighting control unit 23 changes the current value, pulse width and number of pulses of the current to be applied to the light source 34 so that the measured light amount is equal to a currently set light amount. For example, when the illumination light amount is smaller than the set light amount, the lighting control unit 23 increases the current value, pulse width, or number of pulses of the current to be applied to the light source 34 during either the non-all-line exposure period TNL or the all-line exposure period TAL. Further, for example, when the illumination light amount is larger than the set light amount, the lighting control unit 23 decreases the current value, pulse width, or number of pulses of the current to be applied to the light source 34 during either the non-all-line exposure period TNL or the all-line exposure period TAL.

When the processing of step S4 has been performed, the control device 2 next determines whether the set value of the illumination light amount has been changed (step S5). When the difference between the measured light amount and the set light amount is equal to or less than a threshold value (step S3; YES), the control device 2 skips the processing of step S4, and makes a determination in step S5. In step S5, for example, it is determined whether the user has performed an operation of changing the set value of the illumination light amount on the operation unit 24 of the control device 2. When the set value has not been changed (step S5; NO), the control device 2 returns to the processing of step S2. On the other hand, when the set value has been changed (step S5; YES), the control device 2 returns to the processing of step S1. Subsequently, the control device 2 repeats the processing of acquiring a video from the endoscope scope 4 and displaying the acquired video on the display device 5 while repeating the processing of steps S1 to S5.

As described above, in the imaging system 1 according to the present embodiment, the current value, pulse width, number of pulses, etc. of the drive current to be applied to the light source 34 are controlled by using the illumination light amount (measured light amount) measured by the light amount measuring unit 33 in addition to the predetermined control information as shown in FIG. 5. Further, in the imaging system 1 according to the present embodiment, when the illumination light amount is reduced, the current to be applied to the light source 34 during the non-all-line exposure period TNL containing the reading period TTR is controlled so that the pulse width and the number of pulses in the pulse current of a plurality of pulses are changed. As described above, by applying the pulse current of the plurality of pulses to the light source 34 during the non-all-line exposure period TNL, it is possible to prevent deterioration of image quality such as occurrence of fringes.

In the above processing performed by the imaging system 1, the illumination light amount for a subject may be estimated based on the illumination light amount in the light source device 3 measured by the light amount measuring unit 33 (optical sensors 33R, 33G, 33B) and the brightness value of a vide (image) acquired from the endoscope scope 4, and the current to be applied to the light source 34 may be controlled based on the estimation result.

Figure 8A:
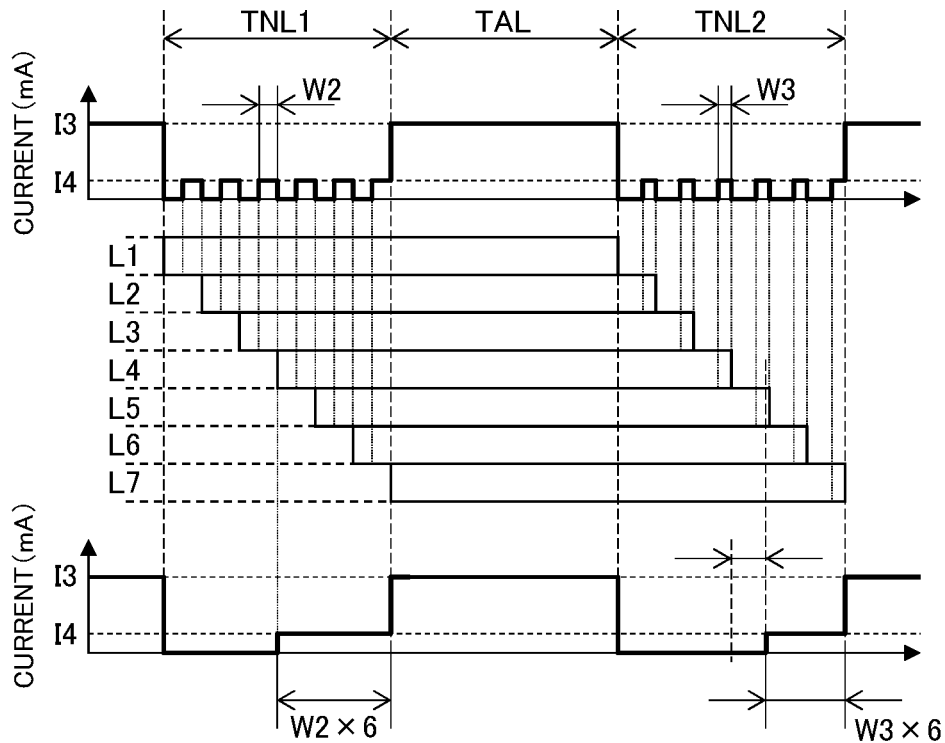
FIGS. 8A and 8B are graphs showing the amount of illumination light for each line when data for one frame of a video are read out.
Figure 8B:
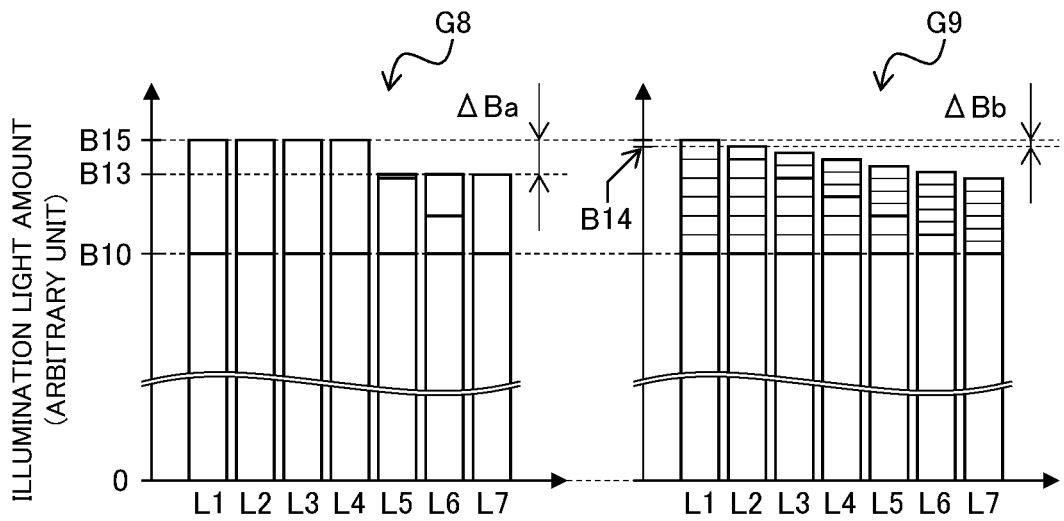

FIGS. 8A and 8B are graphs illustrating the illumination light amount for each line when reading data of one frame of a video. FIG. 8A shows the exposure period for each of seven lines L1 to L7 when the data of one frame of the video is shared to and read out by the seven lines L1 to L7, and two examples of the drive current to be applied to the light source 34. A first example of the drive current shown above the line L1 is an example in which the same drive current as the drive current in the case of the set light amount BS3 described with reference to FIGS. 5 and 6 is applied. In the first example, a pulse current having a plurality of pulses whose pulse number is a maximum number and in which the current value of each pulse is the minimum current value I4 is applied during non-all-line exposure periods TNL1 and TNL2. Further, during the all-line exposure period TAL, a current having the maximum current value of I3 is applied over the entire all-line exposure period TAL. A second example of the drive current shown below the line L7 is an example in which a pulse current of one pulse having the minimum current value I4 which corresponds to the pulse current of the plurality of pulses to be applied during the non-all-line exposure periods TNL1, TNL2 in the first example is applied during the non-all-line exposure periods TNL1, TNL2.

In the first example, with respect to the pulse current of the plurality of pulses to be applied to the light source 34 during the non-all-line exposure period TNL1 which is temporally prior to the all-line exposure period TAL, the number of pulses is six, and the pulse width of each pulse is W2. Therefore, with respect to the pulse current of one pulse to be applied during the non-all-line exposure period TNL1 in the second example, the pulse width of one pulse of the pulse current is set to W2×6 (W2 multiplied by 6). Further, in the first example, with respect to the pulse current of the plurality of pulses to be applied to the light source 34 during the non-all-line exposure period TNL2 which is temporally subsequent to the all-line exposure period TAL, the number of pulses is six, and the pulse width of each pulse is W3 (<W2). Therefore, with respect to the pulse current of one pulse to be applied during the non-all-line exposure period TNL2 in the second example, the pulse width of one pulse of the pulse current is set to W3×6 (W3 multiplied by 6). Note that the pulse currents to be applied during the non-all-line exposure periods TNL1 and TNL2 in the first example and the second example are controlled according to the control method of changing the application start time of the minimum current value I4 when the pulse width is changed based on the set light amount. Therefore, in the second example, a relative time at which the minimum current value I4 is applied within the non-all-line exposure period TNL2 is later by only ΔW than a relative time at which the minimum current value I4 is applied within the non-all-line exposure period TNL1.

FIG. 8B shows a graph G9 illustrating an exposure light amount of each line when the drive current of the first example shown in FIG. 8A is applied to the light source 34, and a graph G8 illustrating an exposure light amount of each line when the drive current of the second example shown in FIG. 8A is applied to the light source 34.

Respective partial light amounts from the light amount 0 to the light amount B10 out of the exposure light amounts of the lines L1 to L7 in the two graphs G8 and G9 are components caused by illumination light emitted from the light source 34 by the maximum current value I3 applied over the entire all-line exposure period TAL.

In the graph shown in FIG. 8A, when the drive current of the second example is applied, the exposure start time of each of the lines L1 to L4 whose exposure start times are first to fourth (in other words, first to fourth in order of reading an electric signal) out of the seven lines L1 to L7 is prior to a start time of application of the minimum current value I4 to the light source 34 in the non-all-line exposure period TNL1 which is temporally prior to the all-line exposure period TAL. Further, the exposure end time (the time when reading of each pixel is started) of each of the lines L1 to L4 is prior to a start time of application of the minimum current value I4 to the light source 34 in the non-all-line exposure period TNL2 which is temporarily subsequent to the all-line exposure period TAL. Therefore, when the drive current of the second example is applied, each of the lines L1 to L4 receives light corresponding to the total amount of illumination light amount emitted by the light source 34 during only the non-all-line exposure period TNL1 out of the non-all-line exposure periods TNL1 and TNL2. Therefore, the exposure light amount of each of the lines L1 to L4 when the drive current of the second example is applied is the sum B15 of a component caused by illumination light emitted from the light source 34 during the non-all-line exposure period TNL1 and a component caused by illumination light emitted from the light source 34 by the maximum current value I3 applied over the entire all-line exposure period TAL.

Further, when the drive current of the second example is applied, the exposure start time of each of the lines L5 to L7 whose exposure start times are fifth to seventh (in other words, fifth to seventh in order of reading an electric signal) out of the seven lines L1 to L7 is subsequent to the start time of application of the minimum current value I4 to the light source 34 in the non-all-line exposure period TNL1, and the exposure end time thereof is subsequent to the start time of application of the minimum current value I4 to the light source 34 in the non-all-line exposure period TNL2. Therefore, the exposure light amount of each of the lines L5 to L7 when the drive current of the second example is applied is the sum of a component caused by illumination light emitted from the light source 34 during the non-all-line exposure period TNL1, a component caused by illumination light emitted from the light source 34 by the maximum current value I3 applied over the entire all-line exposure period TAL, and a component caused by illumination light emitted from the light source 34 during the non-all-line exposure period TNL2.

However, as described above, the relative time at which the application of the minimum current value I4 within the non-all-line exposure period TNL2 is started is later than the relative time at which the application of the minimum current value I4 within the non-all-line exposure period TNL1 is started. Therefore, a period in which each pixel of the lines L5 to L7 receives light corresponding to the illumination light emitted by the light source 34 in the non-all-line exposure periods TNL1 and TNL2 is shorter than a period in which each pixel of the lines L1 to L4 receives light. Therefore, the exposure light amount of each of the lines L5 to L7 when the drive current of the second example is applied is equal to the value B13 which is smaller than the sum B15 of the exposure light amount of each of the lines L1 to L4 as shown in the graph G8. At this time, the difference ΔBa between the sum B15 of the exposure light amount of the line L4 and the sum B13 of the exposure light amount of the line L5 is the value corresponding to the difference (W2−W3)×6 between the pulse width W2×6 of one pulse in the pulse current to be applied during the non-all-line exposure period TNL1, and the pulse width W3×6 of one pulse in the pulse current to be applied during the non-all-line exposure period TNL2.

On the other hand, when the drive current of the first example is applied (that is, when the drive current is applied according to the control method of the present embodiment), as shown in the graph G9, the difference ΔBb in exposure light amount between any two adjacent lines of the lines L1 to L7 is equal to the value corresponding to the difference (W2−W3) between the pulse width W2 of one pulse in the pulse current to be applied during the non-all-line exposure period TNL1 and the pulse width W3 of one pulse in the pulse current to be applied during the non-all-line exposure period TNL2.

In the case where the electric signal of each line is read out in the rolling shutter mode, if the difference in exposure light amount between the two adjacent lines is large, unevenness (stripes) in image quality caused by the difference in exposure light amount occurs at the boundary between the two lines, resulting in deterioration in image quality. This type of deterioration in image quality becomes more remarkable as the difference in exposure light amount between two adjacent lines increases, and in particular, as the ratio of the difference in exposure light amount to the total of the respective exposure light amounts of the lines is greater, the deterioration in image quality is more remarkable. As described above, when the drive current of the first example is applied, the difference ΔBb in exposure light amount between any two adjacent lines is smaller than the difference ΔBa in exposure light amount (about ⅙) between the line L4 and the line L5 when the drive current of the second example is applied. Moreover, when the drive current of the first example is applied, the total of the exposure light amounts of the lines includes a component caused by application of the maximum current value I3 to the light source 34 over the entire all-line exposure period TAL, and the component is remarkably large as compared with the light amount corresponding to the difference in exposure light amount between the line L4 and the line L5 when the driving current of the second example is applied. Therefore, when the drive current of the first example is applied according to the control method described in the present embodiment, it is possible to prevent deterioration in image quality caused by the difference in exposure light amount between the lines as compared with the case where the drive current of the second example is applied.

When a pulse current of a plurality of pulses is applied to the light source 34 during the non-all-line exposure period TNL, the maximum value of the number of pulses can be set to an arbitrary value. As shown in FIGS. 8A and 8B, when the maximum value of the number of pulses is set to a value which is smaller than the number of horizontal lines by only one, the fluctuation in the turn-on period (that is, the exposure period) of pulsed light for each horizontal line is reduced, so that the respective exposure light amounts of the horizontal lines are averaged.

Further, in the drive current control method according to the present embodiment, the minimum current value I4 which is equal to or greater than a minimum current value that assures light emission (emission of illumination light) of the light source 34 is set. When the set illumination light amount is equal to or more than an illumination light amount calculated based on the minimum current value I4 and the exposure period, there is performed current control in which the drive current having the current value determined based on the relations $I_{TNL}$ and $I_{TAL}$ of the current vs. illumination light amount shown in FIG. 5 is applied over the entire exposure period. In other words, this current control is a control operation of applying a pulse current of one pulse which has a pulse width matching the exposure period and has a current value determined based on the relations $I_{TNL}$ and $I_{TAL}$ of the current vs. illumination light amount. When the set illumination light amount is smaller than the illumination light amount calculated based on the minimum current value I4 and the exposure period, the PWM control of controlling the current value, the pulse width, and the number of pulses based on the set illumination light amount is performed. As a result, for example, there occurs no discontinuous change in the emitted light amount caused by the minimum current value which assures the light emission of the light source 34 (emission of the illumination light), so that it is possible to secure a wider dynamic range for the illumination light amount. In particular, in the drive current control method according to the present embodiment, as described above, when the drive current to be applied to the light source 34 during the non-all-line exposure period TNL is PWM-controlled, the PWM control of changing the pulse width in a pulse current of a plurality of pulses is combined with the PWM control of changing the number of pulses in a pulse current in which the pulse width of one pulse is the minimum pulse width. As a result, the magnitude of the illumination light amount when the PWM control is performed can be sequentially changed in a multi-stage manner.

Further, in the drive current control method according to the present embodiment, as described above, the light amount of illumination light emitted by the light source 34 is measured, and the drive current to be applied to the light source 34 can be controlled based on the difference between the measured illumination light amount and the illumination light amount set by the user or the like. In such a control method, for example, when the drive current to be applied to the light source 34 is PWM-controlled, the pulse width and the number of pulses in the drive current (pulse current) can be adjusted to the pulse width and the number of pulses corresponding to the set illumination light amount based on the light amount of pulsed illumination light emitted by the light source 34. Therefore, when the drive current to be applied to the light source 34 is PWM-controlled, the pulse current to be applied can be controlled with high precision according to the light emission characteristics of the light source 34.

Note that the imaging system 1 shown in FIGS. 1 and 2 is merely an example of the imaging system 1 according to the present embodiment. The imaging system 1 according to the present embodiment can be appropriately modified without departing from the subject matter of the present embodiment. For example, in the imaging system 1 according to the present embodiment, a part or the whole of the function of the light source device 3 may be incorporated in the control device 2. Further, the imaging system 1 according to the present embodiment may be a system in which the control device 2, the light source device 3, and the display device 5 are integrated.

As described above, the light source device 3 of the imaging system 1 according to the present embodiment may be a device which has a plurality of light sources, mixes (mixes colors of) respective light pieces emitted by the plurality of light sources, and emits the mixed light as illumination light to the endoscope scope 4. Further, the imaging device using the illumination light emitted by the light source device 3 is not limited to the endoscope scope 4, and may be another imaging device that is capable of imaging a subject in a state where the subject is irradiated with the illumination light emitted by the light source device 3.

Further, in the imaging system 1 of the present embodiment, the maximum number of pulses when a pulse current of a plurality of pulses is applied to the light source 34 during the non-all-line exposure period TNL may be 2 or more, and for example, it may be determined based on the number of lines or the like when an electric signal (video data) of one frame is acquired.

Another exemplary embodiment will be described below with reference to the drawings.

In this embodiment, another example of the control method for the illumination light amount in the imaging system 1 illustrated in the above embodiment will be described.

Figure 9:
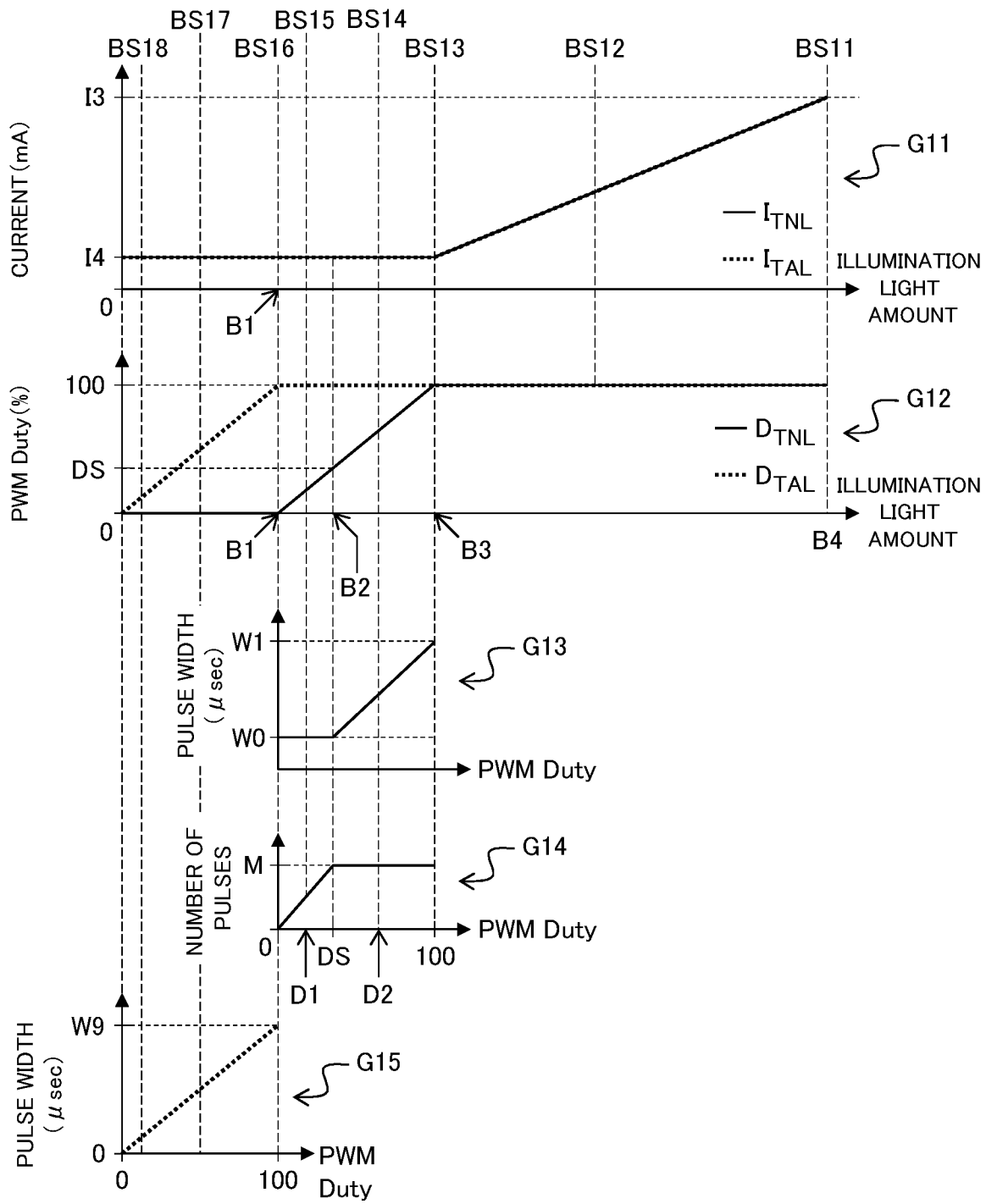
FIG. 9 is a graph showing a method of controlling the amount of illumination light according to an exemplary embodiment.

FIG. 9 is a graph illustrating a control method for an illumination light amount according to the present embodiment.

A graph G11 of the current vs. illumination light amount shown in an uppermost part of FIG. 9 shows the relation between a set value (set light amount) of the illumination light amount set by the user, the control device 2 or the like, and a current to be applied to one of the light sources included in the light source 34 (for example, the red LED 34R of FIG. 3). A relation $I_{TNL}$ indicated by a solid line shows the relation of the drive current to be applied to the light source 34 during the non-all-line exposure period TNL including the reading period TTR. A relation $I_{TAL}$ indicated by a dotted line shows the relation of the drive current to be applied to the light source 34 during the all-line exposure period (non-reading period) TAL.

In the two relations of the relation $I_{TNL}$ and the relation $I_{TAL}$ shown in the graph G11, the relation between the set light amount and the drive current is the same therebetween. In the relation $I_{TNL}$ and the relation $I_{TAL}$, the value of the drive current for the set light amount in the range of a light amount 0 to a third light amount B3 is the minimum current value I4. The third light amount B3 is larger than a first light amount B1 and a second light amount B2 described later, and smaller than a maximum light amount B4. Further, in the relation $I_{TNL}$ and the relation $I_{TAL}$, the value of the drive current for the set light amount in the range of the third light amount B3 to the maximum light amount B4 is proportional to the set light amount in the range of the minimum current value I4 to the maximum current value I3. In other words, as the set light amount approaches the maximum light amount B4, the value of the drive current approaches the maximum current value I3.

In the drive current control method according to the present embodiment, the value of the drive current to be applied to the light source 34 is determined based on the relation $I_{TNL}$ and the relation $I_{TAL}$ shown in the graph G11 as in the case of the control method described in the above embodiment. Further, in the drive current control method according to the present embodiment, the drive current (pulse current) application method is determined based on a graph G12 of the PWM Duty vs. Illumination light amount shown below the graph G11.

The graph 12 of the PWM Duty vs. Illumination light amount illustrates the relation between the set light amount and the duty ratio in PWM control (that is, the percentage of the value obtained by dividing the pulse width of one pulse by the cycle). A relation $D_{TNL}$ indicated by a solid line shows the relation between the set light amount and the duty ratio for the drive current to be applied during the non-all-line exposure period TNL including the reading period TTR. A relation $D_{TAL}$ indicated by a dotted line shows the relation between the set light amount and the duty ratio for the drive current to be applied during the all-line exposure period (non-reading period) TAL.

In the relation $D_{TAL}$ shown in the graph G12, the duty ratio for the set light amount in the range of the first light amount B1 to the maximum light amount B4 is equal to 100%. Further, in the relation $D_{TAL}$ shown in the graph G12, the duty ratio for the set light amount in the range of the light amount 0 to the first light amount B1 is proportional to the set light amount in the range of 0% to 100%. In other words, when the set light amount is within the range of the light amount 0 to the first light amount B1, as the set light amount is closer to the first light amount B1, the value of the duty ratio is larger, and approaches 100%. Therefore, when the set light amount is in the range of the first light amount B1 to the maximum light amount B4, the lighting control unit 23 controls the drive current to be applied to the light source 34 during the all-line exposure period TAL according to the control method of applying a constant current over the entire all-line exposure period TAL. In other words, the lighting control unit 23 sets, as the drive current to be applied to the light source 34 during the all-line exposure period TAL, a pulse current of one pulse which has a current value determined based on the set light amount and the relation $I_{TAL}$ and whose pulse width matches the all-line exposure period TAL.

On the other hand, when the set light amount is in the range of the light amount 0 to the first light amount B1, the lighting control unit 23 controls the drive current to be applied to the light source 34 during the all-line exposure period TAL according to the PWM control. Specifically, the lighting control unit 23 sets, as the drive current to be applied to the light source 34 during the all-line exposure period TAL, a pulse current of one pulse in which the period calculated based on the all-line exposure period TAL and the duty ratio corresponding to the magnitude of the set light amount is the pulse width. The current value of one pulse in this pulse current is the minimum current value I4. With respect to the pulse width, for example, as shown in a graph G15, the pulse width in the case of the light amount 0 is set to 0 μsec, and the pulse width in the case of the first light amount B1 is set to W9 (all-line exposure period TAL), thereby determining the pulse width as being proportional to the set light amount.

On the other hand, in the relation $D_{TNL}$ shown in the graph G12, the duty ratio for the set light amount in the range of the light amount 0 as the minimum value to the first light amount B1 is equal to 0%. Therefore, when the set light amount is in the range of the light amount 0 to the first light amount B1, the lighting control unit 23 applies no drive current to the light source 34 during the non-all-line exposure period TNL. Further, in the relation $D_{TNL}$ shown in the graph G12, the duty ratio for the set light amount in the range of the fourth light amount B3 to the maximum light amount B4 is equal to 100%. Therefore, when the set light amount is in the range of the third light amount B3 to the maximum light amount B4, the lighting control unit 23 controls the drive current to be applied to the light source 34 during the non-all-line exposure period TNL according to the control method of applying a constant current over the entire non-all-line exposure period TNL. In other words, the lighting control unit 23 sets a pulse current of one pulse which has a current value determined based on the set light amount and the relation $I_{TNL}$ and whose pulse width matches the non-all-line exposure period TNL.

Further, in the relation $D_{TNL}$ shown in the graph G12, the duty ratio for the set light amount in the range of the first light amount B1 to the third light amount B3 is proportional to the set light amount in the range of 0% to 100%. Therefore, when the set light amount is in the range of the first light amount B1 to the third light amount B3, the lighting control unit 23 controls the drive current to be applied to the light source 34 during the non-all-line exposure period TNL according to the PWM control. Specifically, the lighting control unit 23 sets, as the drive current to be applied to the light source 34 during the non-all-line exposure period TNL, a pulse current of a plurality of pulses obtained by dividing a period calculated based on the non-all-line exposure period TNL and the duty ratio corresponding to the magnitude of the set light amount into a plurality of periods and setting one period of the plurality of divided periods to a pulse width. The current value of each pulse in the pulse current of the plurality of pulses is set to the minimum current value I4. When the pulse current of the plurality of pulses is applied during the non-all-line exposure period TNL, for example, like two graphs G13 and G14 shown in FIG. 9, the minimum value of the pulse width per pulse and the maximum value of the number of pulses in a pulse current to be applied are preset, and the pulse current is generated based on these settings.

Further, when the drive current to be applied during the non-all-line exposure period TNL is PWM-controlled, as shown in FIG. 9, the control based on the pulse width and the control based on the number of pulses are switched to each other with the second light amount B2 between the first light amount B1 and the third light amount B3 being defined as a boundary. When the set light amount is in the range of the second light amount B2 to the third light amount B3, the lighting control unit 23 sets the number of pulses to the maximum value and increases or decreases the pulse width according to the magnitude of the set light amount. When the set light amount is in the range of the first light amount B1 to the second light amount B2, the lighting control unit 23 sets the pulse width to the minimum value and increases or decreases the number of pulses according to the magnitude of the set light amount.

As described above, in the drive current control method according to the present embodiment, when the set light amount is larger than the third light amount B3, the drive currents having the same current value are applied to the light source 34 over the entire non-all-line exposure period TNL and during the entire all-line exposure period TAL, respectively. When the set light amount is in the range of the first light amount B1 to the third light amount B3, the drive current to be applied to the light source 34 during the non-all-line exposure period TNL is controlled according to the PWM control, and the drive current to be applied to the light source 34 during the all-line exposure period TAL is controlled according to the control of applying the minimum current value I4 over the entire all-line exposure period TAL.

Figure 10:
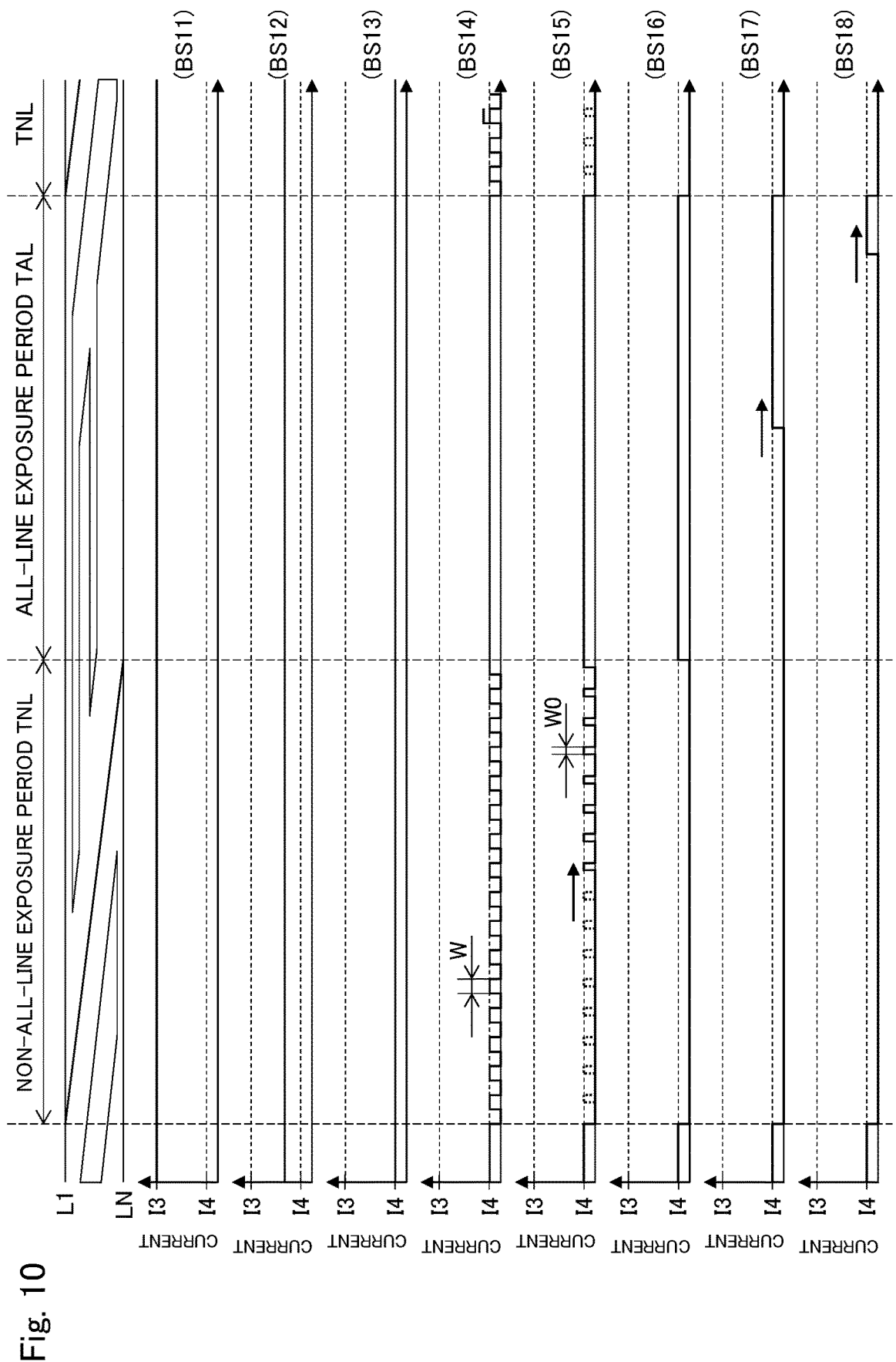
FIG. 10 is a graph showing the relation between the amount of illumination light and a current applying method.

FIG. 10 is a graph illustrating the relation between the illumination light amount and the current application method according to the present embodiment. Note that FIG. 10 shows an example of the drive current to be applied to the light source 34 when each of set light amounts BS11 to BS18 shown in FIG. 9 is set. Here, each of the set light amounts BS11 to BS18 may be an illumination light amount set by a method such as operating the operation unit 24 of the control device 2 by the user of the imaging system 1, or may be an illumination light amount measured by the light amount measuring unit 33, or an illumination light amount which is set by the lighting control unit 23 based on the brightness (luminance) or the like of the video notified from the video processing unit 22.

The set light amount BS11 is the maximum light amount B4, and each of the duty ratios of the PWM control for the drive current to be applied during the non-all-line exposure period TNL and during the all-line exposure period TAL is equal to 100%. Therefore, as shown in FIG. 10, in the case of the set light amount BS11, the lighting control unit 23 sets, as the drive currents to be applied to the light source 34 during the non-all-line exposure period TNL and during the all-line exposure period TAL, a current having the maximum current value I3 to be applied over each of the entire periods TNL and TAL (a pulse current of one pulse whose pulse width matches each period).

The set light amount BS12 is smaller than the maximum light amount B4 and larger than the third light amount B3. Therefore, each of the duty ratios of the PWM control for the drive current to be applied during the non-all-line exposure period TNL and during the all-line exposure period TAL is equal to 100%. Further, the values of the drive currents to be applied during the non-all-line exposure period TNL and during the all-line exposure period TAL are the same value which is smaller than the maximum current value I3 and larger than the minimum current value I4. Therefore, as shown in FIG. 10, in the case of the set light amount BS12, the lighting control unit 23 sets, as the drive currents to be applied to the light source 34 during the non-all-line exposure period TNL and during the all-line exposure period TAL, a drive current which applies a current having a current value determined based on the set light amount to the light source 34 over each of the entire periods TNL and TAL (a pulse current of one pulse whose pulse width matches each period). The current value of this drive current is smaller than the maximum current value I3 and larger than the minimum current value I4.

The set light amount BS13 is the third light amount B3. Therefore, each of the duty ratios of the PWM control for the drive currents to be applied during the non-all-line exposure period TNL and during the all-line exposure period TAL is equal to 100%. Further, each of the values of the drive currents to be applied during the non-all-line exposure period TNL and during the all-line exposure period TAL is the minimum current values I4. Therefore, as shown in FIG. 10, in the case of the set light amount BS13, the lighting control unit 23 sets a current having the minimum current value I4 to be applied over each of the entire periods TNL and TAL as the drive currents to be applied to the light source 34 during the non-all-line exposure period TNL and during the all-line exposure period TAL.

The set light amount BS14 is larger than the second light amount B2 and smaller than the third light amount B3. Therefore, the duty ratio of PWM control for the all-line exposure period TAL is equal to 100%. On the other hand, the duty ratio of PWM control for the non-all-line exposure period TNL is smaller than 100% and larger than the threshold value DS. Further, each of the values of the drive currents to be applied during the non-all-line exposure period TNL and the all-line exposure period TAL is the minimum current value I4. Therefore, as shown in FIG. 10, in the case of the set light amount BS14, the lighting control unit 23 sets, as the drive current to be applied to the light source 34 during the non-all-line exposure period TNL, a pulse current of a plurality of pulses in which the number of pulses is a maximum number M and the pulse width per pulse is a pulse width corresponding to the set light amount BS14 (a pulse width larger than the minimum width W0 and smaller than the maximum width W1). The current value of each pulse in the pulse current of the plurality of pulses is set to the minimum current value I4. Further, the lighting control unit 23 sets a current having the minimum current value I4 to be applied over the entire all-line exposure period TAL as the drive current to be applied to the light source 34 during the all-line exposure period TAL.

Further, the pulse current to be applied during the non-all-line exposure TNL when the set light amount is larger than the set light amount BS14 and smaller than the third light amount B3 is a pulse current in which the number of pulses is identical to that of the pulse current shown in FIG. 10 and the pulse width of one pulse is larger than W. Further, the pulse current to be applied during the non-all-line exposure period TNL when the set light amount is smaller than the set light amount BS14 and larger than the second light amount B2 is a pulse current in which the number of pulses is identical to that of the pulse current shown in FIG. 10 and the pulse width of one pulse is smaller than W.

The set light amount BS15 is smaller than the second light amount B2 and larger than the first light amount B1. Therefore, the duty ratio of PWM control for the all-line exposure period TAL is equal to 100%. On the other hand, the duty ratio of PWM control for the non-all-line exposure period TNL is smaller than the threshold value DS and larger than 0%. Further, the values of the drive currents to be applied during the non-all-line exposure period TNL and during the all-line exposure period TAL are the minimum current value I4. Therefore, as shown in FIG. 10, in the case of the set light amount BS15, the lighting control unit 23 sets, as the drive current to be applied to the light source 34 during the non-all-line exposure period TNL, a pulse current in which the pulse width per pulse is the minimum pulse width W0 and the number of pulses corresponds to the set light amount BS15. The current value of each pulse in this pulse current is set to the minimum current value I4. Further, the lighting control unit 23 sets a current having the minimum current value I4 to be applied over the entire all-line exposure period TAL as the drive current to be applied to the light source 34 during the all-line exposure period TAL.

Further, the pulse current to be applied during the non-all-line exposure period TNL when the set light amount is larger than the set light amount BS15 and smaller than the second light amount B2 is a pulse current whose pulse width is identical to the pulse width (minimum value W0) of the pulse current shown in FIG. 10 and the number of pulses is large. Further, the pulse current to be applied during the non-all-line exposure period TNL when the set light amount is smaller than the set light amount BS15 and larger than the first light amount B1 is a pulse current in which the pulse width is identical to the pulse width (minimum value W0) of the pulse current shown in FIG. 10, and the number of pulses is small.

The set light amount BS16 is the first light amount B1. Therefore, the duty ratio of PWM control for the all-line exposure period TAL is equal to 100%, whereas the duty ratio of PWM control for the non-all-line exposure period TNL is equal to 0%. Further, the values of the drive currents to be applied during the non-all-line exposure period TNL and during the all-line exposure period TAL are the minimum current value I4. Therefore, as shown in FIG. 10, in the case of the set light amount BS16, the lighting control unit 23 determines that a pulse current in which the pulse width per pulse is a minimum width and the number of pulses is equal to 0 is applied to the light source 34 during the non-all-line exposure period TNL (that is, no drive current is applied to the light source 34 during the non-all-line exposure period TNL). Further, the lighting control unit 23 sets a current having the minimum current value I4 to be applied over the all-line exposure period TAL as the drive current to be applied to the light source 34 during the all-line exposure period TAL.

The set light amount BS17 is smaller than the first light amount B1 and larger than the light amount 0. In the case of the set light amount BS17, the duty ratio of PWM control for the non-all-line exposure period TNL is equal to 0%. Therefore, as shown in FIG. 10, in the case of the set light amount BS17, the lighting control unit 23 determines that no drive current is applied to the light source 34 during the non-all-line exposure period TNL. Further, in the case of the set light amount BS17, the duty ratio of PWM control for the all-line exposure period TAL is a value smaller than 100% and larger than 0%. Therefore, as shown in FIG. 10, in the case of the set light amount BS17, the lighting control unit 23 sets a pulse current of one pulse having a pulse width determined based on the all-line exposure period TAL and the duty ratio as the drive current to be applied to the light source 34 during the all-line exposure period TAL. The current value in this pulse current of one pulse is set to the minimum current value I4. The duty ratio corresponding to the set light amount BS17 in FIG. 9 is equal to about 50%. Therefore, in the case of the set light amount BS17, the pulse width in the pulse current of one pulse to be applied to the light source 34 during the all-line exposure period TAL is set to about half the time of the all-line exposure period TAL.

When the set light amount is larger than the set light amount BS17 and smaller than the first light amount B1, the pulse width in the pulse current of one pulse to be applied to the light source 34 during the all-line exposure period TAL is set to be larger than the pulse width in the case of the set light amount BS17. Further, when the set light amount is smaller than the set light amount BS17 and larger than the light amount 0 (for example, in the case of the set light amount BS18), the pulse width in the pulse current of one pulse to be applied to the light source 34 during the all-line exposure period TAL is set to be smaller than the pulse width in the set light amount BS17.

As described above, in the drive current control method according to the present embodiment, when the drive current is applied to the light source 34 based on the set light amount, the drive current to be applied to the light source 34 (that is, illumination light to be emitted by the lighting unit 31) is variably controlled in at least a part of the non-all-exposure period TNL containing the reading period TTR. Further, in the drive current control method according to the present embodiment, the drive current to be applied to the light source 34 (that is, illumination light to be emitted by the lighting unit 31) can also be variably controlled in at least a part of the all-line exposure period TAL other than the non-all-line exposure period TNL. Further, in the drive current control method according to the present embodiment, the pulse width and the number of pulses in the pulse current to be applied to the light source 34 can be controlled, for example, based on the illumination light amount measured by the light amount measuring unit 33.

In the drive current control method according to the present embodiment, as described above, when the set light amount is larger than the third light amount B3, the drive current to be applied during the non-all-line exposure period TNL and the drive current to be applied during the all-line exposure period TAL are set to drive currents having the same current value. Therefore, as compared with the control method as described in the above embodiment, control information (the content of processing) when a current having a predetermined current value is applied over the entire non-all-line exposure period TNL and the entire all-line exposure period TAL is simplified. For example, in the drive current control method according to the present embodiment, the range of the set light amount in which the current value of the drive current to be applied to the light source 34 varies (switches) at the boundary between the non-all-line exposure period TNL and the all-line exposure period TAL is narrower than the range in the control method described in the above embodiment. Therefore, in the drive current control method according to the present embodiment, the frequency of the switching operation in the circuit (drive unit 35) for generating the drive current to be applied to the light source 34 can be reduced, and the processing load can be reduced.

In the drive current control method according to the present embodiment, as described above, the current value of the drive current to be applied to the light source 34 during the non-all-line exposure period TNL is identical to the current value of the drive current to be applied to the light source 34 during the all-line exposure period TAL. Therefore, the amount of illumination light to be emitted by the light source 34 during the non-all-line exposure period TNL can be estimated from the amount of illumination light measured during the all-line exposure period TAL. For example, when the drive current to be applied to the light source 34 during the non-all-line exposure period TNL is PWM-controlled, the measurement of the illumination light amount is calculated by adding (integrating) the light amounts of respective pulses in the illumination light (pulsed light) emitted by the light source 34. Therefore, when the current value or the pulse width of a current to be applied for pulsed light to be emitted by the light source 34 is small, a measurement error may become large (the measurement accuracy may deteriorate). On the other hand, in the drive current control method according to the present embodiment, the illumination light amount can be measured in the all-line exposure period TAL by using illumination light which is continuously emitted by the light source 34 for a period sufficiently longer than the pulse width in the non-all-line exposure period TNL. Therefore, in the drive current control method according to the present embodiment, the pulse width and the number of pulses in the PWM control to be performed during the non-all-line exposure period TNL can be controlled with higher accuracy.

A further exemplary embodiment will now be described with reference to the drawings.

In this embodiment, still another example of the method of controlling the illumination light amount in the imaging system 1 illustrated in the above embodiment will be described.

Figure 11:
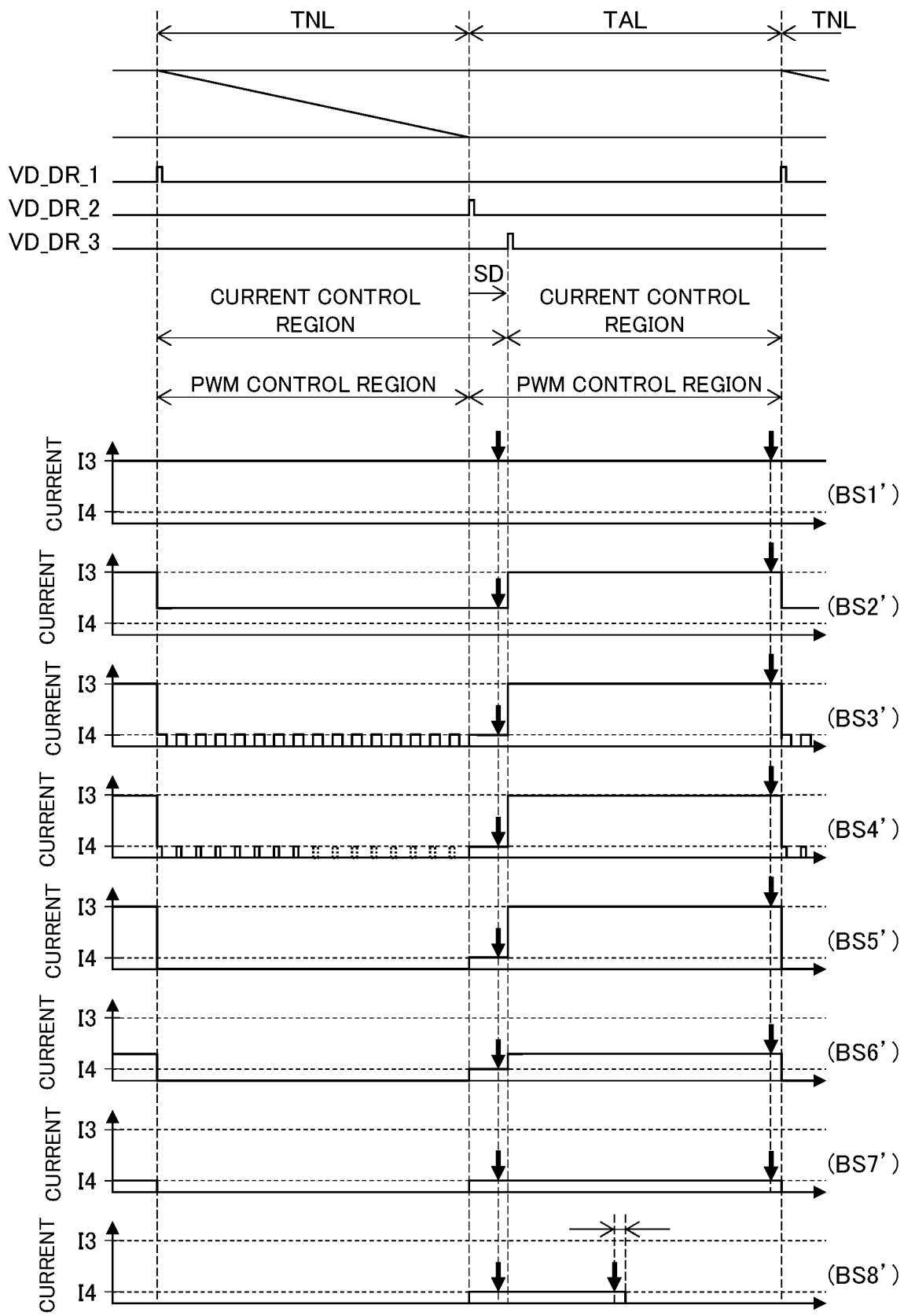
FIG. 11 is a graph showing a method of controlling the amount of illumination light according to an exemplary embodiment.

FIG. 11 is a graph illustrating a method of controlling the illumination light amount according to this embodiment. The graph shown in FIG. 11 shows a drive current to be applied to the light source 34 when the control method of the present embodiment is applied to the method of determining the current value, the pulse width, and the number of pulses in each of the set light amounts BS1 to BS8 shown in FIG. 5. BS1' to BS8' in the graph of FIG. 11 correspond to the set light amounts BS1 to BS8 of FIG. 5, respectively.

In the method of controlling the illumination light amount according to the present embodiment, as shown in FIG. 11, an initial period SD having a predetermined time length containing a start time of an all-line exposure period TAL is set within all-line exposure period TAL. The initial period SD is provided to measure the light amount of illumination light emitted by the light source 34 during the non-all-line exposure period TNL which is temporally prior to the all-line exposure period TAL containing the initial period SD.

The current value of the current to be applied to the light source 34 during the initial period SD within the all-line exposure period TAL depends on whether the current to be applied to the light source 34 during the period TAL is PWM-controlled. When the PWM control is not performed during the all-line exposure period TAL, the current value of the current to be applied to the light source 34 during the initial period SD is affected by the current value of the current to be applied to the light source 34 during the non-all-line exposure period TNL which is temporally prior to the period TAL. When the control of the current to be applied to the light source 34 during the non-all-line exposure period TNL is not the PWM control, but the control (current control) of applying a current having a current value larger the minimum current value I4 to the light source 34 over the entire period TNL, the current to be applied to the light source 34 during the initial period SD following the period TNL is set to a current having the same current value as the current applied to the light source 34 during the non-all-line exposure period TNL. When the current to be applied to the light source 34 during the non-all-line exposure period TNL is controlled by the PWM control, or when no current is applied to the light source 34 over the entire period TNL, the current to be applied to the light source 34 during the initial period SD following the period TNL is set to a current having the minimum current value I4. On the other hand, when the PWM control is performed during the all-line exposure period TAL, the current value of the current to be applied to the light source 34 during the initial period SD depends on the pulse width determined based on the set light amount and the position of the pulse within the all-line exposure period TAL.

VD_DR_1, VD_DR_2, and VD_DR_3 shown in FIG. 11 are trigger signals for switching the above-mentioned non-all-line exposure period TNL, all-line exposure period TAL, and initial period SD. The trigger signal VD_DR_1 is a signal for notifying a timing of switching from the all-line exposure period TAL to the non-all-line exposure period TNL (that is, the start of the non-all-line exposure period TNL). The trigger signal VD_DR_2 is a signal for notifying a timing of switching from the non-all-line exposure period TNL to the all-line exposure period TAL (that is, the start of the initial period SD). The trigger signal VD_DR_3 is a signal for notifying an end timing of the initial period SD.

In the case of the set light amount BS1 shown in FIG. 5, the duty ratio of PWM control for the all-line exposure period TAL is equal to 100% as described above. Therefore, in the case of the set light amount BS1, the current to be applied to the light source 34 during the all-line exposure period TAL is controlled not by the PWM control, but by the control of applying a current having a current value corresponding to the set light amount over the entire period TAL. Therefore, the current to be applied to the light source 34 during the initial period SD within the all-line exposure period TAL is a current having a current value identical to that of the current applied to light source 34 during the non-all-line exposure period TNL which is temporally prior to the initial period SD (that is, a current having the maximum current value I3) as in the case of the set light amount BS1' shown in FIG. 11. Further, in the control method of the present embodiment, a current having a current value corresponding to the current value determined based on the set light amount and the duty ratio of PWM control (that is, a current having the maximum current value I3) is applied to the light source 34 for a remaining period after the initial period SD in the all-line exposure period TAL has elapsed.

In the case of the set light amount BS2 shown in FIG. 5, the duty ratio of PWM control for the all-line exposure period TAL is equal to 100% as described above. Therefore, in the case of the set light amount BS2, the current to be applied to the light source 34 during the all-line exposure period TAL is controlled not by the PWM control, but by the control of applying a current having a current value corresponding to the set light amount over the entire period TAL. Further, in the case of the set light amount BS2, the current value of the current to be applied to the light source 34 during the non-all-line exposure period TNL is smaller than the maximum current value I3 and larger than the minimum current value I4. Therefore, the current to be applied to the light source 34 during the initial period SD within the all-line exposure period TAL is a current having a current value identical to that of the current applied to the light source 34 during the non-all-line exposure period TNL which is temporally prior to the initial period SD (that is, a current having a current value smaller than the maximum current value I3) as in the case of the set light amount BS2' shown in FIG. 11. Then, the current having the maximum current value I3 is applied to the light source 34 for a remaining period after the initial period SD in the all-line exposure period TAL has elapsed.

In the case of the set light amount BS3 shown in FIG. 5, the duty ratio of PWM control for the all-line exposure period TAL is equal to 100% as described above. Therefore, in the case of the set light amount BS3, the current to be applied to the light source 34 during the all-line exposure period TAL is controlled not by the PWM control, but by the control (current control) of applying a current having a current value corresponding to the set light amount over the entire period TAL. Further, in the case of the set light amount BS3, the current to be applied to the light source 34 during the non-all-line exposure period TNL is controlled by the PWM control. Therefore, the current to be applied to the light source 34 during the initial period SD within the all-line exposure period TAL is a current having a current value identical to that of the current applied to the light source 34 during the non-all-line exposure period TNL which is temporally prior to the initial period SD (that is, a current having the minimum current value I4) as in the case of the set light amount BS3' shown in FIG. 11. Then, the current having the maximum current value I3 is applied to the light source 34 for the remaining period after the initial period SD in the all-line exposure period TAL has elapsed. Likewise, in the case of the set light amount BS4 shown in FIG. 5, the current to be applied to the light source 34 during the initial period SD within the all-line exposure period TAL is a current having a current value identical to that of the current applied to the light source 34 during the non-all-line exposure period TNL which is temporally prior to the initial period SD (that is, a current having the minimum current value I4) as in the case of the set light amount BS4' shown in FIG. 11. Then, the current having the maximum current value I3 is applied to the light source 34 for a remaining period after the initial period SD in the all-line exposure period TAL has elapsed.

In the case of the set light amount BS5 shown in FIG. 5, the duty ratio of PWM control for the all-line exposure period TAL is equal to 100% as described above. Therefore, in the case of the set light amount BS5, the current to be applied to the light source 34 during the all-line exposure period TAL is controlled not by the PWM control, but the control (current control) of applying a current having a current value corresponding to the set light amount over the entire period TAL. Further, in the case of the set light amount BS5, the current to be applied to the light source 34 during the non-all-line exposure period TNL is controlled by the PWM control, but as shown in FIG. 5, the number of pulses in the case of the set light amount BS5 is equal to 0. Therefore, in the case of the set light amount BS5, the current to be applied to the light source 34 during the non-all-line exposure period TNL is a pulse current in which the number of pulses is equal to 0, and no current is applied over the entire non-all-line exposure period TNL as in the case of the set light amount BS5' shown in FIG. 11. However, as shown in FIG. 5, the current value corresponding to the set light amount BS5 is the minimum current value I4 larger than 0. Therefore, in the case of the set light amount BS5, as indicated as the set light amount BS5' in FIG. 11, the current to be applied to the light source 34 during the initial period SD is a current having the minimum current value I4. Then, a current having the maximum current value I3 is applied to the light source 34 for a remaining period after the initial period SD in the all-line exposure period TAL has elapsed.

In the case of the set light amount BS6 shown in FIG. 5, the duty ratio of PWM control for the all-line exposure period TAL is equal to 100% as described above. Therefore, in the case of the set light amount BS6, the current to be applied to the light source 34 during the all-line exposure period TAL is controlled not by the PWM control, but the control (current control) of applying a current having a current value corresponding to the set light amount over the entire period TAL. Further, in the case of the set light amount BS6, since the duty ratio of PWM control for the non-all-line exposure period TNL is equal to 0%, no current is applied to the light source 34 over the entire period TNL. Therefore, in the case of the set light amount BS6, as indicated as the set light amount BS6' in FIG. 11, the current to be applied to the light source 34 during the initial period SD is a current having the minimum current value I4. Further, the current value corresponding to the set light amount BS6 is smaller than the maximum current value I3 and larger than the minimum current value I4. Then, a current having a current value smaller than the maximum current value I3 and larger than the minimum current value I4 is applied to the light source 34 for a remaining period after the initial period SD in the all-line exposure period TAL has elapsed.

In the case of the set light amount BS7 shown in FIG. 5, the duty ratio of PWM control for the all-line exposure period TAL is equal to 100% as described above. Therefore, in the case of the set light amount BS7, the current to be applied to the light source 34 during the all-line exposure period TAL is controlled not by the PWM control, but the control (current control) of applying a current having a current value corresponding to the set light amount over the entire period TAL. Further, in the case of the set light amount BS7, since the duty ratio of PWM control for the non-all-line exposure period TNL is equal to 0%, no current is applied to the light source 34 over the entire period TNL. Therefore, in the case of the set light amount BS7, as indicated as the set light amount BS7' in FIG. 11, the current to be applied to the light source 34 during the initial period SD is a current having the minimum current value I4. Further, the current value during the all-line exposure period TAL corresponding to the set light amount BS7 is the minimum current value I4. Therefore, a current having the minimum current value I4 is also applied to the light source 34 for a remaining period after the initial period SD in the all-line exposure period TAL has elapsed.

In the case of the set light amount BS8 shown in FIG. 5, as described above, the duty ratio of PWM control for the all-line exposure period TAL is smaller than 100% and larger than 0%. Therefore, in the case of the set light amount BS8, the current to be applied to the light source 34 during the all-line exposure period TAL is controlled by the PWM control. Further, in the case of the set light amount BS8, since the duty ratio of PWM control for the non-all-line exposure period TNL is equal to 0%, no current is applied to the light source 34 over the entire period TNL. Therefore, in the case of the set light amount BS8, for example, as indicated as the set light amount BS8' in FIG. 11, the current to be applied to the light source 34 during the initial period SD is a current having the minimum current value I4. Note that in FIG. 11, when the current to be applied to the light source 34 during the all-line exposure period TAL is PWM-controlled, the time at which the application of the current is started is fixed to a start time of the all-line exposure period TAL (initial period SD), and the time at which the application of the current is finished is changed, whereby the pulse width of the applied pulse current is changed to a pulse width corresponding to the set light amount. Therefore, even when the current to be applied during the all-line exposure period TAL is a pulse current, it is possible to measure the light amount of illumination light emitted by the light source 34 within the initial period SD.

Note that the time length of the initial period SD can be set to, for example, an arbitrary time length that is not less than the maximum value W1 of the pulse width of one pulse when the current to be applied to the light source 34 during the non-all-line exposure period TNL is PWM-controlled. The time length of the initial period SD is set to be several times as long as the maximum value W1 of the pulse width of one pulse, whereby the illumination light amount corresponding to the pulse current to be applied to the light source 34 during the non-all-line exposure period TNL can be detected accurately. Further, the ratio of the initial period SD to the all-line exposure period TAL is kept to be a low value, whereby it is possible to increase the total amount (integral value) of the current to be applied to the light source 34 during the non-all-line exposure period TNL when the current to be applied to the light source 34 during the non-all-line exposure period TNL is PWM-controlled. Therefore, as described with reference to FIG. 8, deterioration of image quality caused by the difference in exposure time between two adjacent lines can be prevented.

Further, when the current value of the current to be applied to the light source 34 changes in the middle of the all-line exposure period TAL as in the case of the control method for the illumination light amount according to the present embodiment, for example, as shown in FIG. 11, the light amount of illumination light emitted by the light source 34 may be measured shortly before the application of the current to the light source 34 during the all-line exposure period TAL is finished (for example, at a timing indicated by a downward arrow). In this way, the light amount of illumination light in the non-all-line exposure period TNL can be measured immediately after starting the application of the current to the light source 34 in the all-line exposure period TAL, and the light amount of illumination light in the period TAL can be measured immediately before the application of the current to the light source 34 in the all-line exposure period TAL is finished. Therefore, for example, it is possible to suppress the increase in difference between the illumination light amount after the change and the set light amount due to changing the current value of the current to be applied to the light source 34 in the middle of the all-line exposure period TAL.

A further exemplary embodiment will now be described with reference to the drawings.

Figure 12:
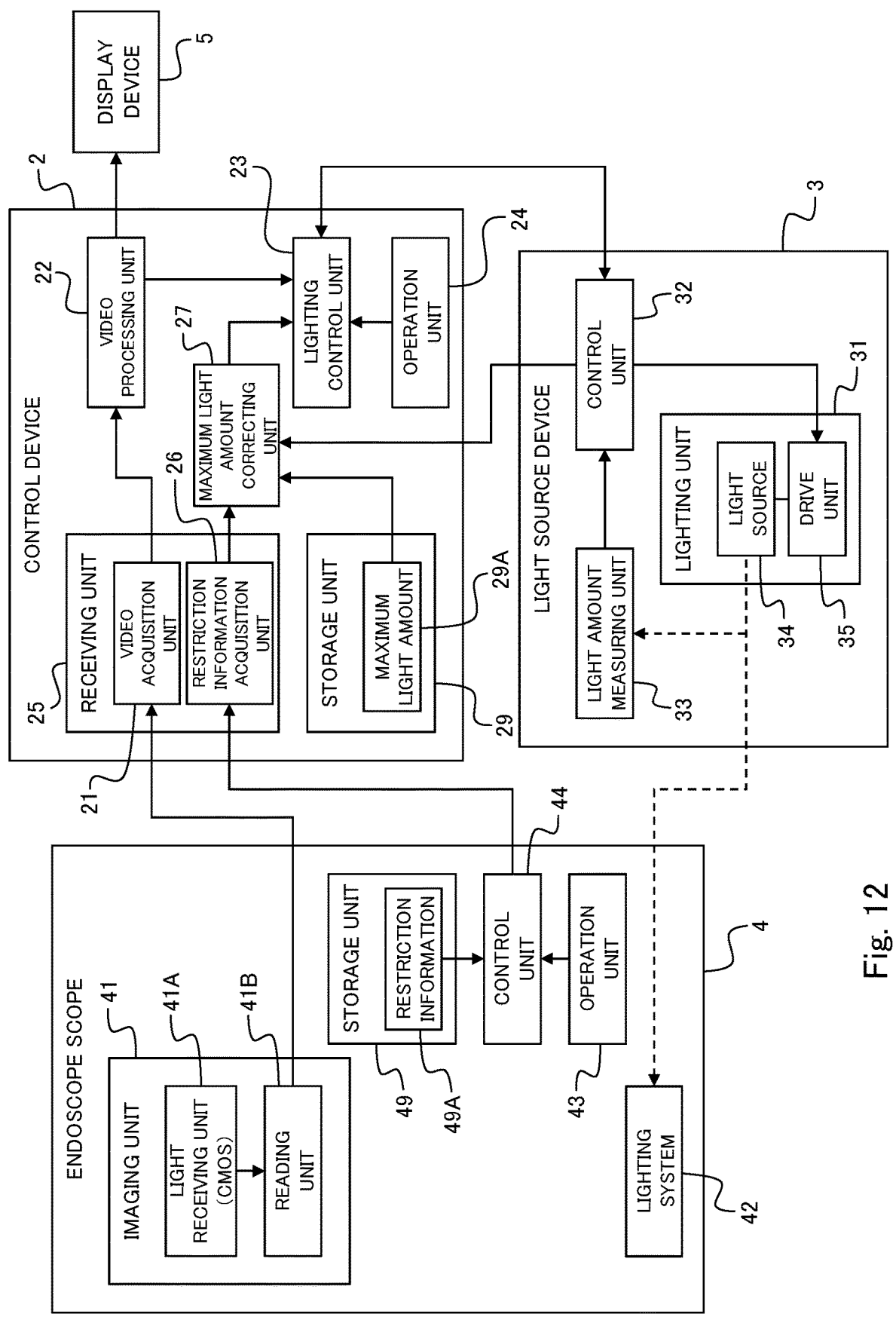
FIG. 12 is a diagram showing a functional block of an imaging system according to an exemplary embodiment.

FIG. 12 is a diagram showing a functional block of an imaging system according to this embodiment. The imaging system 1 shown in FIG. 12 is an endoscope system similar to the imaging system 1 (see FIG. 1) described in the above embodiment, and includes a control device 2, a light source device 3, an endoscope scope 4, and the display device 5.

The control device 2 in the imaging system 1 of the present embodiment includes a receiving unit 25, a video processing unit 22, a lighting control unit 23, an operation unit 24, a maximum light amount correction unit 27, and a storage unit 29. Further, the light source device 3 of the imaging system 1 includes a lighting unit 31, a control unit 32, and a light amount measuring unit 33. Further, the endoscope scope 4 of the imaging system 1 includes an imaging unit 41, a lighting system 42, an operation unit 43, a control unit 44, and a storage unit 49. Among functional blocks in the imaging system 1 of the present embodiment, detailed description on functional blocks having functions equivalent to those of the functional blocks described in the above embodiment will be omitted in the following description.

The receiving unit 25 of the control device 2 includes a video acquisition unit 21 and a restriction information acquisition unit 26. As described in the above embodiment, the video acquisition unit 21 acquires an electric signal indicating a video of a subject captured by the imaging unit 41 of the endoscope scope 4. The restriction information acquisition unit 26 acquires restriction information 49A stored in the storage unit 49 of the endoscope scope 4. The restriction information 49A is information indicating, for example, an illumination light amount at which the temperature of a tip portion (a portion where the imaging unit 41 and the lighting system 42 are arranged) under the operation of the endoscope scope 4 increases to a predetermined temperature (permissible temperature) or higher.

The maximum light amount correction unit 27 of the control device 2 corrects the maximum value of the light amount of illumination light emitted by the light source 34 of the lighting unit 31 of the light source device 3 based on the restriction information acquired by the restriction information acquisition unit 26 and maximum light amount information 29A stored in the storage unit 29. The maximum light amount information 29A is information indicating the maximum light amount in the light source 34 of the light source device 3 which is used in combination with the control device 2, and it is stored in the storage unit 29 of the control device 2 at the time of shipment of the imaging system 1, for example. The maximum light amount correction unit 27 corrects the maximum value of the light amount of illumination light (maximum light amount) to be provided from the light source device 3 to the endoscope scope 4 so that the maximum light amount is corrected from the maximum value of an illumination light amount which can be emitted by the light source 34 to a value which is determined based on the restriction information acquired from the endoscope scope 4 so as to cause the temperature of the tip portion of the endoscope scope 4 to fall in a permissible temperature range.

The lighting control unit 23 of the control device 2 controls the light amount of illumination light to be emitted by the lighting unit 31 of the light source device 3 based on a set value of the luminosity of illumination light (set light amount) input by a user's operation on the operation unit 24 and the light amount of illumination light to the subject. Note that when the maximum light amount of the illumination light is corrected by the maximum light amount correction unit 27, the lighting control unit 23 in the imaging system 1 of the present embodiment controls the light amount of the illumination light based on the corrected maximum light amount.

As described above, the endoscope scope 4 in the imaging system 1 of the present embodiment includes the imaging unit 41, the lighting system 42, the operation unit 43, the control unit 44, and the storage unit 49. The control unit 44 of the endoscope scope 4 according to the present embodiment reads out restriction information 49A stored in the storage unit 49 and transmits the control information to the control device 2, for example, when the endoscope scope 4 is connected to the control device 2 or when the operation of the imaging system 1 is started or the like.

During operation, the tip portion of the endoscope scope 4 generates heat as illumination light passes through the lighting system 42, resulting in rising of the temperature. When the temperature of the tip portion rises, the operating characteristic of the imaging unit 41 fluctuates, and the difference between information on the color or the like of the subject in a read-out electrical signal (video data) and the actual color or the like of the subject may become large.

Further, the operating characteristic of the tip portion of the endoscope scope 4 with respect to the temperature differs depending on the type of the endoscope scope 4. Therefore, in an imaging system 1 in which plural types of endoscope scopes 4 different in model number, specification or the like can be used properly, the temperature characteristic of the tip portion of the endoscope scope 4 with respect to the temperature differs depending on the type of the endoscope scope 4 using the control device 2 and the light source device 3 in combination with each other. Therefore, when the maximum light amount of illumination light to be provided to the endoscope scope 4 during operation is the maximum light amount of illumination light that can be emitted by the light source device 3 (for example, the illumination light amount B5 in FIG. 5), the temperature of the tip portion of the endoscope scope 4 increases to a permissible temperature or more, which may cause a risk that image quality deteriorates. Therefore, in the imaging system 1 of the present embodiment, the light amount of illumination light to be emitted by the light source 34 is controlled under a condition that the temperature of the tip portion of the endoscope scope 4 is within a permissible range in light of the operating characteristic of the endoscope scope 4.

FIG. 13 is a diagram illustrating an example of a control method for the maximum light amount of illumination light to be emitted by the light source. FIG. 13 shows examples of the upper limit of the permissible temperature, the temperature of the tip portion when illumination light having a maximum light amount BM that can be emitted by the light source 34, the light source device 3 is provided, the magnitude relation between the two temperatures, the maximum value BX of the illumination light amount during operation, and the maximum value I of a current to be applied to the light source in each of two types of endoscope scopes 4. Here, for the sake of simplicity of description, it is assumed that the light source 34 of the light source device 3 is one light source that emits light of a predetermined color (wavelength range).

The endoscope scope 4 of the first type A has the magnitude relation of TA>TMA between the upper limit TA of the permissible temperature and the temperature TMA of the tip portion when the illumination light having the maximum light amount BM that can be emitted by the light source device 3 is provided. In such a case, the temperature of the tip portion when the endoscope scope 4 is operated while the illumination light having the maximum light amount BM which can be emitted by the light source device 3 is provided to the endoscope scope 4 is equal to the upper limit of the permissible temperature or less. Therefore, in the case of use of the endoscope scope 4 of the first type A, even when the maximum light amount BX of illumination light to be provided to the endoscope scope 4 is set to the maximum light amount BM of illumination light that can be emitted by the light source device 3, deterioration in image quality or the like which is caused by rise of temperature hardly occurs. Therefore, in the imaging system 1 using the endoscope scope 4 of the first type A, when the set light amount is the maximum light amount (for example, the illumination light amount B5 or the like in FIG. 5), a current having the maximum current value I3 is applied to the light source 34.

On the other hand, the endoscope scope 4 of the second type B has the magnitude relation of TMB>TB between the upper limit TB of the permissible temperature and the temperature TMB at the tip portion when the illumination light having the maximum light amount BM that can be emitted by the light source device 3 is provided. In such a case, the temperature of the tip portion when the endoscope scope 4 is operated while the illumination light of the maximum light amount BM which can be emitted by the light source device 3 is provided to the endoscope scope 4 exceeds the upper limit of the permissible temperature. Therefore, in the case of use of the endoscope scope 4 of the second type B, when the maximum light amount BX of illumination light to be provided to the endoscope scope 4 is set to the maximum light amount BM of illumination light that can be emitted by the light source device 3, there is a risk that deterioration in image quality or the like caused by rise of temperature occurs. Therefore, in the imaging system 1 using the endoscope scope 4 of the second type B, when the set light amount is the maximum light amount (for example, the illumination light amount B5 in FIG. 5), a current having a current value I5 (I3>I5>I4) is applied to the light source 34 so that the magnitude relation between the maximum light amount BX of illumination light to be provided to the endoscope scope 4 and the maximum light amount BM of illumination light that can be emitted by the light source device 3 satisfies BM>BX. As a result, the temperature of the tip portion of the endoscope scope 4 can be prevented from exceeding an upper limit temperature at which a normal operation is ensured in the imaging system 1 using the endoscope scope 4 of the second type B, and deterioration in image quality or the like caused by rise of temperature can be prevented.

Figure 14:
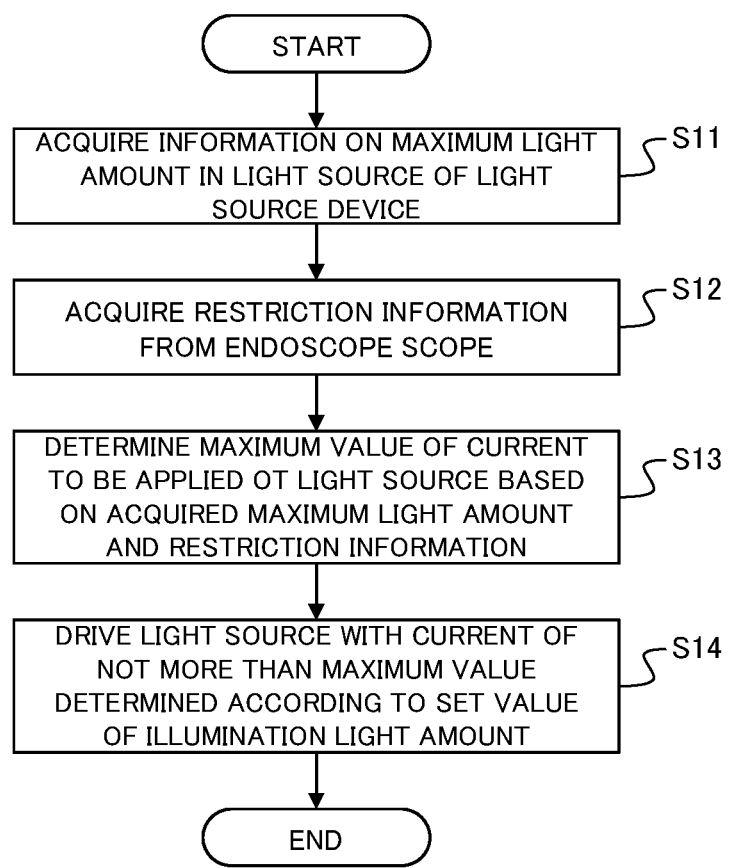
FIG. 14 is a flowchart showing an example of processing to be performed by the imaging system.

FIG. 14 is a flowchart illustrating an example of processing to be performed by the imaging system according to the present embodiment. FIG. 14 shows a flowchart of processing for controlling the current to be applied to the light source 34, which includes processing for restricting the maximum light amount based on the type of the endoscope scope 4.

First, the control device 2 of the imaging system 1 acquires information on the maximum light amount BM in the light source 34 of the light source device 3 (step S11), and also acquires the restriction information 49A from the endoscope scope 4 (step S12). The information on the maximum light amount BM in the light source 34 is acquired, for example, by the maximum light amount correction unit 27 of the control device 2 reading out maximum light amount information 29A stored in the storage unit 29. The maximum light amount information 29A is stored in the storage unit 29, for example, when a pair of a control device 2 and a light source device 3 to be used in combination with the control device 2 are shipped. Further, the restriction information 49A is acquired by the maximum light amount correction unit 27 via the control information acquisition unit 26.

Next, the control device 2 determines the maximum value of a current to be applied to the light source based on the acquired maximum light amount and restriction information (step S13). The processing of step S13 is performed by the maximum light amount correction unit 27. The maximum light amount correction unit 27 determines the maximum value of the current to be applied to the light source 34 based on the magnitude relation between the maximum light amount BX of illumination light in the endoscope scope 4 which is specified by the restriction information acquired from the endoscope scope 4, and the maximum light amount BM of illumination light that can be emitted by the light source 34 of the light source device 3. Here, the maximum light amount BX of illumination light in the endoscope scope 4 is the maximum value of an illumination light amount that does not exceed the upper limit of a permissible temperature range in which the endoscope scope 4 is ensured to operate stably. When the magnitude relation of the maximum light amount satisfies BXBM, the maximum light amount correction unit 27 sets, as the maximum value of the current to be applied to the light source 34, a current value corresponding to the maximum light amount BM of illumination light that the light source 34 can emit (for example, the current value I3 shown in FIG. 5 and the like). On the other hand, when the magnitude relation of the maximum light amount satisfies BX<BM, the maximum light amount correction unit 27 sets, as the maximum value of the current to be applied to the light source 34, a current value corresponding to the maximum light amount BX of illumination light in the endoscope scope 4 (for example, the current value I5 satisfying the relation of I3>I5>I4 with the current values I3 and I4 shown in FIG. 5 and the like). The maximum light amount correction unit 27 notifies the lighting control unit 23 of the set maximum value of the current.

Thereafter, the control device 2 drives the light source 34 with a current of the set maximum value or less according to the set value of the illumination light amount (step S14). The processing of step S14 is performed by the lighting control unit 23. For example, when the maximum value of the current notified from the maximum light amount correction unit 27 is a current value when the light source 34 emits illumination light having the maximum light amount that can be emitted by the light source 34 (for example, the maximum current value I3 shown in FIG. 5 and the like), the lighting control unit 23 controls the illumination light amount with the current value in the case of emitting the illumination light having the maximum light amount that can be emitted by the light source 34 being set as the maximum current of the current to be applied to the light source 34. On the other hand, when the maximum value of the current notified from the maximum light amount correction unit 27 is smaller than the current value in the case of emitting the illumination light having the maximum light amount that can be emitted by the light source 34, the lighting control unit 23 corrects the maximum value of the current to be applied to the light source 34 to the maximum value of the current notified from the maximum light amount correction unit, and then controls the illumination light amount. In this case, for example, the lighting control unit 23 changes the maximum value of the current to be applied to the light source 34 in the graph G1 shown in FIG. 5 and the graph G11 shown in FIG. 9 from I3 to I5 (I3>I5>I4), and then controls the current to be applied to the light source 34 according to the method as described above.

As described above, in the imaging system 1 of the present embodiment, the maximum light amount of the illumination light to be provided from the light source device 3 to the endoscope scope 4 can be restricted so that the temperature of the tip portion of the endoscope scope 4 under operation is within the permissible temperature range. Therefore, it is possible to prevent fluctuation or the like in output performance of the imaging unit 41 (light receiving unit 41A) which is caused by rise of temperature at the tip portion of the endoscope scope 4, and it is possible to prevent deterioration in image quality and the like. Therefore, the imaging system 1 of the present embodiment can prevent deterioration in image quality caused by the difference in exposure light amount among lines when an electric signal is read out from the light receiving unit 41A in the rolling shutter mode, and can prevent deterioration in image quality caused by operation failure or the like due to the temperature rise of the tip portion.

Further, in the imaging system 1 of the present embodiment, the maximum light amount of illumination light to be provided from the light source device 3 to the endoscope scope 4 can be restricted based on the restriction information 49A which is stored in the storage unit 49 of the endoscope scope 4 and set according to each type of the endoscope scope 4. Therefore, even when the endoscope scope 4 to be used in combination with the pair of the control device 2 and the light source device 3 is changed according to the type of a subject to be imaged, the maximum light amount of illumination light to be provided from the light source device 3 to the endoscope scope 4 can be properly controlled (corrected) based on the restriction information 49A of the changed endoscope scope 4.

Further, although detailed description will be omitted, when the light source 34 includes a plurality of light sources (for example, the red LED 34R, the green LED 34G, and the blue LED 34B in FIG. 3), the maximum light amount of illumination light to be provided from the light source device 3 to the endoscope scope 4 and the maximum light amount of each light source are determined based on the light amount of each component of light to be provided to the endoscope scope 4 under the condition that the color (color temperature) of illumination light to be applied to a subject is irradiated is within a predetermined range, and then controls the current to be applied to each light source. Further, in the endoscope scope 4 to be used in combination with the light source device 3 having a plurality of light sources, restriction information of the maximum light amount for the illumination light to be emitted by each of the plurality of light sources may be stored as the restriction information 49A in the storage unit 49. In this case, for example, the control device 2 may acquire restriction information for illumination light of a color having the largest maximum light amount among restriction information of the maximum light amount for illumination light of a plurality of colors included in the restriction information 49A, and control the light amount of illumination light to be provided from the light source device 3 to the endoscope scope 4 based on the acquired restriction information.

Note that the functional configurations of the control device 2, the light source device 3, and the endoscope scope 4 shown in FIG. 12 are merely examples of the functional configurations of the respective devices in the imaging system 1 of the present embodiment. The functional configurations of the control device 2, the light source device 3, and the endoscope scope 4 of the imaging system 1 according to the present embodiment can be appropriately changed without departing from the subject matter of the present embodiment. Further, the flowchart of FIG. 14 is merely an example of the processing to be performed by the control device 2 in the imaging system 1 of the present embodiment. The processing to be performed by the control device 2 according to the present embodiment can be appropriately changed without departing from the subject matter of the present embodiment. For example, when the maximum light amount of illumination light to be provided to the endoscope scope 4 is restricted (lowered) based on the restriction information 49A of the endoscope scope 4, the brightness of an image (video) acquired from the endoscope scope 4 decreases by only a restricted amount. Therefore, when the maximum amount of illumination light to be provided to the endoscope scope 4 is restricted, the brightness of the image acquired from the endoscope scope 4 may be corrected (gained up) based on the amount of change in illumination light amount caused by the restriction. In this case, for example, the maximum light amount correction unit 27 also notifies the video processing unit 22 of the maximum value of the current determined in the processing of step S13 of the flowchart of FIG. 14. Further, in the imaging system 1 according to the present embodiment, for example, instead of restricting the maximum light amount of illumination light based on the restriction information 49A prestored in the storage unit 49 of the endoscope scope 4, the endoscope scope 4 may be provided with a temperature sensor at the tip portion of the endoscope scope 4 to dynamically control (restrict) the maximum light amount of illumination light based on the temperature detected by the temperature sensor.

As described above, the control device 2 in the imaging system 1 exemplified in the above embodiments is not limited to dedicated hardware, and may be a device for causing a general-purpose computer such as a personal computer to execute a control program that includes a process for controlling the drive current applied to the light source as described above.

Figure 15:
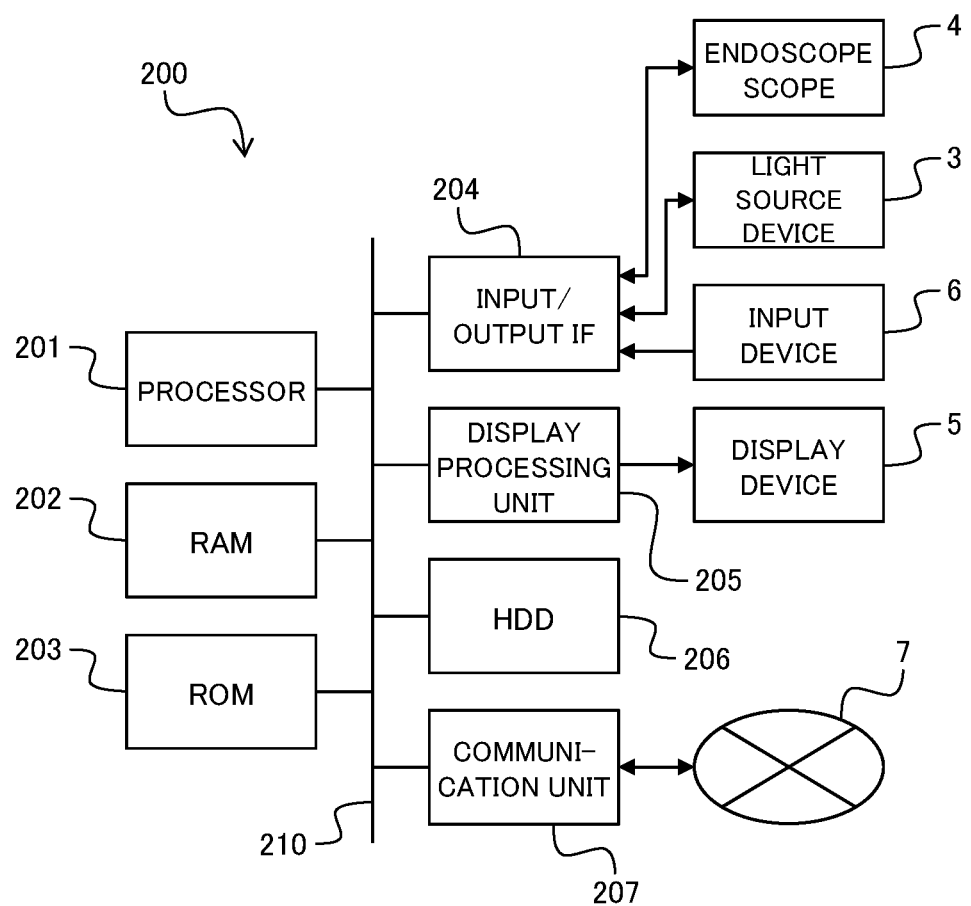
FIG. 15 is a diagram showing a hardware configuration of a computer.

FIG. 15 is a diagram showing a hardware configuration of a computer. A computer 200 as the control device 2 includes a processor 201, a random access memory (RAM) 202, a read only memory (ROM) 203, an input/output IF (Interface) 204, a display processing unit 205, a hard disk drive (HDD) 206, a communication unit 207, a bus 210, a display device 5, and an input device 6.

The processor 201 is an arithmetic processing unit such as a central processing unit (CPU), reads a control program from the ROM 203, and executes various control processing according to the read control program. The RAM 202 is a work area for temporarily storing various data such as the control program and an electric signal (video data) related to a video from the endoscope scope 4. The RAM 202 is, for example, a dynamic random access memory (DRAM). The ROM 203 is a non-volatile storage unit for storing the control program, various data, and the like. The ROM 203 is, for example, a flash memory.

The input/output IF 204 transmits/receives data to/from external devices. The external devices are, for example, an input device 6 such as a keyboard or a touch panel, the light source device 3, and the endoscope scope 4. The display processing unit 205 generates a display image and outputs it to the display device 5 such as a liquid crystal display. The ROM 203 and the HDD 206 constitute the storage unit 29 of the control device 2. The processor 201 is connected to the RAM 202, the ROM 203, etc. via the bus 210.

The communication unit 207 connects the communication network 7 such as the Internet or a local area network (LAN) to the computer 200 so as to be communicable therebetween.

The video acquisition unit 21, the video processing unit 22, and the lighting control unit 23 of the control device 2 are implemented through software processing by the processor 201 or the like. Further, the operation unit 24 of the control device 2 is implemented, for example, by the input device 6 connected through the input/output IF 204.

The present disclosure is not limited to the above-described embodiments as they are, and can be embodied by modifying the components within a scope that does not depart from the subject matter at the implementation stage. Further, various embodiments can be formed by an appropriate combination of the plurality of components disclosed in the above-described embodiments. For example, all the components shown in the embodiments may be combined as appropriate. In addition, components across different embodiments may be combined as appropriate. It goes without saying that such various modifications and applications can be made without departing from the disclosed subject matter.

What is claimed is:

1. An imaging system comprising:
   a light source configured to emit illumination light with which a subject is irradiated;
   an image sensor in which pixels for generating electric signals by receiving light from the subject and performing photoelectric conversion on the received light are arranged two-dimensionally;
   a reading circuit configured to sequentially read out the electrical signals from horizontal lines of the pixels in the image sensor on a horizontal-line basis during a reading period for each frame or each field period;
   an optical sensor configured to measure an amount of the illumination light emitted by the light source; and
   a lighting controller configured to control independently:
   emission of the illumination light in a non-all-line exposure period, which contains the reading period for one frame or one field period and in which at least one horizontal line of the horizontal lines for the one frame or the one field period is not exposed to light, such that the amount of the illumination light is controlled by repeating turn-on and turn-off of a plurality of pulsed lights and adjusting at least one of a turn-on period and a turn-on frequency of each pulsed light, and
   emission of the illumination light in an all-line exposure period, in which all of the horizontal lines for the one frame or the one field period are exposed to light, such that the amount of the illumination light is controlled while maintaining a state in which the illumination light is emitted over an entirety of the all-line exposure period.

2. The imaging system according to claim 1, wherein
   when a period for turning off the pulsed light ends, the lighting controller is configured to increase the amount of the illumination light by increasing a current to be applied to the light source during the non-all-line exposure period, and
   when a period for turning on the pulsed light ends, the lighting controller is configured to decrease the amount of the illumination light by decreasing the current to be applied to the light source during the all-line exposure period or shortening a time for which the current is applied to the light source during the all-line exposure period.

3. The imaging system according to claim 1, further comprising a drive circuit configured to drive the light source, wherein the lighting controller is configured to:
   control the amount of the illumination light during the non-all-line exposure period by controlling a current to be applied to the light source by the drive circuit during the non-all-line exposure period such that the current is:
   (i) larger than a lower limit current value at which the drive is enabled to drive the light source or (ii) larger than a minimum current value at which light emission of the light source is ensured, and
   reduce the turn-on frequency of the pulsed light when the turn-on period of the pulsed light is a lower limit time at which the drive circuit is enabled to drive the light source.

4. The imaging system according to claim 1, wherein the lighting controller is configured to set a current to be applied to the light source during the all-line exposure period and a current to be applied to the light source during the non-all line exposure period so that the current to be applied during the all-line exposure period and the current to be applied during the non-all line exposure period have the same current value.

5. The imaging system according to claim 4, wherein the lighting controller is configured to control the current to be applied to the light source during the non-all-line exposure period following the all-line exposure period based on the amount of the illumination light measured by the optical sensor during the all-line exposure period.

6. The imaging system according to claim 1, wherein the lighting controller is configured to set a current to be applied to the light source during an initial period which includes a start time of the all-line exposure period and is shorter than the all-line exposure period so that the current has the same current value as a current to be applied during the non-all-line exposure period.

7. The imaging system according to claim 6, wherein the initial period is longer than the turn-on period of the pulsed light in the non-all-line exposure period.

8. The imaging system according to claim 6, wherein when the light source is turned off over an entirety of the non-all-line exposure period, the lighting controller is configured to set the current to be applied to the light source during the initial period so that the current has the same current value as a current to be applied to the light source when the turn-on and turn-off of the plurality of pulsed lights are repeated during the non-all-line exposure period.

9. The imaging system according to claim 6, wherein the lighting controller is configured to control a current to be applied to the light source during a period after lapse of the initial period such that the current to be applied during the period after the lapse of the initial period is not less than the current value of the current to be applied during the initial period.

10. The imaging system according to claim 6, wherein the lighting controller is configured to set a current to be applied to the light source during a period after lapse of the initial period so that the current is larger than the current to be applied to the light source during the initial period.

11. The imaging system according to claim 6, wherein the optical sensor is configured to measure the amount of the illumination light during the initial period, and the lighting controller is configured to control a current to be applied to the light source during the non-all-line exposure period following the all-line exposure period based on the amount of the illumination light measured by the optical sensor during the initial period.

12. The imaging system according to claim 6, wherein the optical sensor is configured to measure the amount of the illumination light in a period after lapse of the initial period, and the lighting controller is configured to control a current to be applied to the light source during the all-line exposure period subsequent to the all-line exposure period based on the amount of the illumination light measured during the period after lapse of the initial period.

13. The imaging system according to claim 1, wherein the lighting controller is configured to control a current to be applied to the light source so that the amount of the illumination light within the all-line exposure period in the one frame or the one field period is equal to or more than the amount of the illumination light within the non-all-line exposure period.

14. The imaging system according to claim 1, wherein when a maximum value of the turn-on frequency of the pulsed light during the non-all-line exposure period is set to a value which is smaller than a number of the horizontal lines by one, and the turn-on frequency of the pulsed light is set to the maximum value, the controller is configured to control the emission of the illumination light such that the turn-on and turn-off of the pulsed light are repeated at equal intervals over an entirety of the non-all-line exposure period.

15. The imaging system according to claim 1, wherein the lighting controller is further configured to:
  determine a maximum light amount of the illumination light to be emitted by the light source based on restriction information indicating a maximum light amount of the illumination light set for the image sensor and the reading circuit, and a maximum amount of illumination light which can be emitted by the light source, and
  control a current to be applied to the light source based on a current value corresponding to a set light amount of the illumination light and the maximum light amount of the illumination light.

16. The imaging system according to claim 15, wherein the restriction information includes information indicating the maximum light amount of the illumination light corresponding to an upper limit of a permissible temperature range set based on operating characteristics related to temperatures of the image sensor and the reading circuit.

17. The imaging system according to claim 1, further comprising:
  a temperature sensor configured to measure a temperature of the image sensor; and
  an endoscope controller configured to generate restriction information including information on the measured temperature;
  wherein the lighting controller is configured to:
  correct a maximum light amount of the illumination light to be emitted by the light source based on the restriction information, and
  control a current to be applied to the light source based on a current value corresponding to a set light amount of the illumination light and a current value corresponding to the corrected maximum light amount of the illumination light.

18. The imaging system according to claim 17, wherein the restriction information includes information indicating whether the measured temperature is greater than a threshold value, and when the measured temperature is greater than the threshold value, the lighting controller is configured to reduce the maximum light amount of the illumination light to be smaller than a maximum light amount that can be controlled in the lighting controller.

19. An endoscope system comprising:
  an endoscope including an image sensor in which pixels for generating electric signals by receiving light from a subject and performing photoelectric conversion on the received light are arranged two-dimensionally, and a reading circuit configured to sequentially read out the electric signals from horizontal lines of the pixels in the image sensor on a horizontal-line basis during a reading period for each frame or each field period;
  a light source device that is configured to provide illumination light to the endoscope and includes a light source configured to emit the illumination light with which the subject is irradiated, and an optical sensor configured to measure an amount of the illumination light emitted by the light source; and
  a control device that is configured to control an amount of the illumination light to be emitted by the light source based on an image of the subject corresponding to the electric signals acquired from the endoscope and the measured amount of the illumination light emitted by the light source which is acquired from the light source device,
  wherein the control device comprises a lighting controller that is configured to control independently:
  emission of the illumination light in a non-all-line exposure period which contains the reading period for one frame or one field period and in which at least one horizontal line of the horizontal lines for the one frame or the one field period is not exposed to light such that the amount of the illumination light is controlled by repeating turn-on and turn-off of a plurality of pulsed lights and adjusting at least one of a turn-on period and a turn-on frequency of each pulsed light, and
  emission of the illumination light in an all-line exposure period in which all of the horizontal lines for the one frame or the one field period are exposed to light such that the amount of the illumination light is controlled while maintaining a state in which the illumination light is emitted over an entirety of the all-line exposure period.

20. A light source device comprising:
  a light source configured to emit illumination light with which a subject is irradiated; and
  a light source controller configured to control a drive current to be applied to the light source independently during a reading period in which accumulated electric signals for one frame are read out on a horizontal-line basis and during a non-reading period in which read-out is not performed, in an imaging device for imaging the subject irradiated with the illumination light;
  wherein, when controlling the drive current during the non-reading period, the light source controller is configured to apply one pulse current and control a current value in the pulse current to be constant; and
  when controlling the drive current during the reading period, the light source controller is configured to apply a plurality of pulse currents and control at least one of a pulse width in the plurality of pulse currents and a number of pulses in the plurality of pulse currents.

21. A method for controlling a light source device for irradiating a subject with illumination light, comprising:
  controlling via a light source controller a drive current to be applied to a light source independently during a reading period in which accumulated electric signals for one frame are read out on a horizontal-line basis and during a non-reading period in which read-out is not performed, in an imaging device for imaging the subject irradiated with the illumination light;
  wherein:
  when controlling the drive current during the non-reading period, the light source controller applies one pulse current and controls a current value in the pulse current to be constant; and
  when controlling the drive current during the reading period, the light source controller applies a plurality of pulse currents and controls at least one of a pulse width in the plurality of pulse currents and a number of pulses in the plurality of pulse currents.

* * * * *